United States Patent
Van Hoe

(10) Patent No.: US 9,977,958 B2
(45) Date of Patent: May 22, 2018

(54) METHOD AND SYSTEM FOR ASSISTING DETERMINATION OF A MEDICAL CONDITION

(71) Applicant: GRAIN IP, Aalst (BE)

(72) Inventor: Lieven Van Hoe, Aalst (BE)

(73) Assignee: GRAIN IP, Aalst (BE)

( * ) Notice: Subject to any disclaimer, the term of this patent is extended or adjusted under 35 U.S.C. 154(b) by 51 days.

(21) Appl. No.: 15/119,849

(22) PCT Filed: Feb. 26, 2015

(86) PCT No.: PCT/EP2015/054059
§ 371 (c)(1),
(2) Date: Aug. 18, 2016

(87) PCT Pub. No.: WO2015/128429
PCT Pub. Date: Sep. 3, 2015

(65) Prior Publication Data
US 2017/0220860 A1  Aug. 3, 2017

(30) Foreign Application Priority Data
Feb. 26, 2014  (WO) ................. PCT/EP2014/053741

(51) Int. Cl.
*G06K 9/00* (2006.01)
*G06F 19/00* (2018.01)

(52) U.S. Cl.
CPC ....... *G06K 9/00463* (2013.01); *G06F 19/321* (2013.01); *G16H 50/20* (2018.01); *G06K 2209/05* (2013.01); *G06K 2209/27* (2013.01)

(58) Field of Classification Search
CPC .......... G06K 9/00463; G06K 2209/05; G06K 2209/27; G06F 19/321; G06F 19/345
See application file for complete search history.

(56) References Cited

U.S. PATENT DOCUMENTS 6,032,678 A    3/2000  Rottem
8,548,828 B1 * 10/2013  Longmire .............. G06Q 10/10
                                                            705/3

(Continued)

FOREIGN PATENT DOCUMENTS

WO   WO 2006/058738      6/2006

OTHER PUBLICATIONS

International Search Report for PCT/EP2015/054059 dated Jun. 15, 2015, 4 pages.

(Continued)

*Primary Examiner* — Shefali Goradia
(74) *Attorney, Agent, or Firm* — Nixon & Vanderhye P.C.

(57) ABSTRACT

The present invention relates to a method for assisting a user in determining a medical condition in a subject from one or more medical images by presenting the user with a list of questions, LOQ, about the subject that are to be answered with an affirmative indication (Y), a negative indication (N) or an unknown indication (X) by input by the user. In response to receiving an answer to one question, the method presents the user with a ranked list of conditions, LOC, and also with an updated LOQ wherein at least the answered question has been removed i.e. the LOQ iteratively collapses or reduces in length. An earlier step of selecting a foundation observation, FO, about the subject reduces the initial LOQ and the possible conditions.

22 Claims, 19 Drawing Sheets

(56) References Cited

U.S. PATENT DOCUMENTS

| | | | |
|---|---|---|---|
| 9,043,217 B2* | 5/2015 | Cashman | E04H 3/08 |
| | | | 705/2 |
| 9,536,052 B2* | 1/2017 | Amarasingham | G06F 19/345 |
| 2012/0101846 A1* | 4/2012 | Gotthardt | G06F 19/322 |
| | | | 705/3 |
| 2013/0253940 A1 | 9/2013 | Zziwa | |

OTHER PUBLICATIONS

Written Opinion of the ISA for PCT/EP2015/054059 dated Jun. 15, 2015, 7 pages.
International Preliminary Report on Patentability for PCT/EP2015/054059 dated Jun. 13, 2016, 7 pages.
Reply to Written Opinion for PCT/EP2015/054059, dated Apr. 20, 2016 with amended claims, 11 pages.

* cited by examiner

FIG. 1

| | | R1 | R2 | R3 | R4 | R5 | R6 | R7 | R8 | R9 | R10 |
|---|---|---|---|---|---|---|---|---|---|---|---|
| Conditions (10) | C1 | L | A | – | – | K | – | – | V | – | – |
| | C2 | A | L | L | K | – | L | U | – | – | – |
| | C3 | – | – | – | – | – | – | – | P | P | – |
| | C4 | U | – | – | U | – | – | – | – | – | U |
| | C5 | – | – | V | P | – | – | K | L | K | – |
| Principal Observations (20) | O1 | Y | – | – | – | Y | N | – | – | N | – |
| | O2 | – | N | – | Y | – | – | – | – | – | N |
| | O3 | – | Y | – | – | Y | – | – | – | Y | – |
| | O4 | – | – | N | – | – | N | – | N | – | – |
| | O5 | – | – | – | Y | N | – | – | – | – | Y |
| | O6 | N | – | Y | – | – | – | – | Y | – | – |
| | O7 | – | – | – | Y | – | – | Y | – | N | – |
| | O8 | – | – | – | – | – | N | – | – | – | – |
| | O9 | – | – | Y | – | – | – | Y | – | Y | – |

FIG. 2

| | | R1 | R2 | | | R5 | | | R8 | |
|---|---|---|---|---|---|---|---|---|---|---|
| | C1 | L | A | – | – | K | – | – | V | – |
| Principal observations | O1 | Y | – | – | – | Y | N | – | – | N |
| | O2 | – | N | – | Y | – | – | – | – | – |
| | O3 | – | Y | – | – | Y | – | – | – | Y |
| | O4 | – | – | N | – | – | N | – | N | – |
| | O5 | – | – | – | Y | N | – | – | – | – |
| | O6 | N | – | Y | – | – | – | – | Y | – |
| | O7 | – | – | – | Y | – | – | Y | – | N |
| | O8 | – | – | – | – | – | N | – | – | – |
| | O9 | – | – | Y | – | – | – | Y | – | Y |

A1

| LFO |
|-----|
| F1  |
| F2  |
| F3  |
| F4  |
| F5  |
| F6  |
| F7  |
| F9  |

|  |  | Rules |  |  |  |  |  |  |  |  |  |  |  |  |  |  |  |  |  |  |  | FO/APR |  |  |
|---|---|---|---|---|---|---|---|---|---|---|---|---|---|---|---|---|---|---|---|---|---|---|---|---|
|  |  | R1 | R2 | R3 | R4 | R6 | R7 | R8 | R9 | R10 | R11 | R12 | R13 | R14 | R15 | R16 | R17 | R18 | R19 | R20 | RX.. | F1 | F2 | FX.. |
| Conditions | C1 | P | V | L | A | A | - | - | - | - | A | - | A | - | A | - | L | V | - | - |  | R |  |
|  | C2 | - | - | - | V | L | P | - | - | P | - | V | - | L | - | K | - | - | V | U |  | O | - |  |
|  | C3 | L | - | A | - | L | U | - | L | - | K | - | - | - | L | - | U | - | - | U |  | O | O |  |
|  | C4 | - | - | - | - | - | - | - | - | A | - | A | - | L | - | V | - | - | - | - |  | - | - |  |
|  | C5 | - | V | - | - | - | P | K | - | U | - | - | - | U | - | - | - | K | P | - |  | O | O |  |
|  | C6 | K | P | U | - | - | - | - | - | U | P | - | - | U | - | - | - | - | - | - |  | R | R |  |
|  | C7 | U | - | - | - | - | - | - | - | - | - | - | P | - | - | - | - | - | - | U |  |  |  |  |
|  | C8 | - | L | - | - | - | - | V | U | P | - | - | - | - | V | K | - | L | - | - |  | O | C |  |
|  | C9 | V | - | - | - | K | - | - | P | - | P | - | - | - | - | - | P | - | P | - |  | C | - |  |
|  | CX.. |  |  |  |  |  |  |  |  |  |  |  |  |  |  |  |  |  |  |  |  |  |  |  |
|  |  |  |  |  |  |  |  |  |  |  |  |  |  |  |  |  |  |  |  |  |  | FO |  |  |
| Principal Observations | O1 | - | - | N | - | - | - | - | N | - | - | Y | - | N | - | - | N | - | N |  |  |  |  |  |
|  | O2 | - | - | - | - | - | - | - | - | - | - | - | - | - | Y | - | - | - | - |  |  | F3 |  |  |
|  | O3 | N | - | - | N | N | - | Y | - | - | Y | Y | - | N | - | N | - | N | - | - |  |  |  |  |
|  | O4 | N | - | - | - | Y | Y | - | - | - | - | Y | - | - | - | - | - | - | - | - |  | F5 |  |  |
|  | O5 | N | - | - | N | - | - | - | - | Y | - | - | - | - | - | - | - | - | - | N |  | F4 |  |  |
|  | O6 | - | N | - | - | - | - | N | N | - | - | N | - | - | N | - | - | N | N | - |  |  |  |  |
|  | O7 | - | - | - | - | - | - | - | - | - | - | - | - | N | - | - | Y | - | - | - |  | F7 |  |  |
|  | O8 | - | - | - | Y | - | Y | Y | - | Y | - | - | - | - | - | - | - | - | - | - |  |  |  |  |
|  | O9 | N | - | - | - | Y | - | - | - | Y | - | N | - | - | - | - | - | - | - | - |  | F1 |  |  |
|  | O10 | - | Y | N | - | - | - | - | Y | - | - | - | - | - | - | - | - | - | Y | - |  |  |  |  |
|  | O11 | Y | N | - | - | - | - | Y | - | - | - | - | - | - | - | - | - | - | - | - |  |  |  |  |
|  | O12 | - | - | - | - | - | N | - | - | Y | N | - | - | - | - | Y | - | - | - |  | F6 |  |  |  |
|  | O13 | N | - | - | Y | - | N | N | - | - | - | - | - | - | - | - | - | Y | - | - |  |  |  |  |
|  | O14 | - | - | - | - | - | Y | - | - | - | - | N | - | - | - | - | - | - | - | - |  |  |  |  |
|  | O15 | N | - | Y | - | Y | N | - | Y | - | Y | - | Y | - | Y | - | Y | - | Y | - |  | F2 |  |  |
|  | O16 | - | - | - | N | Y | - | - | Y | Y | - | Y | N | Y | - | - | - | - | - | - |  |  |  |  |
|  | OX |  |  |  |  |  |  |  |  |  |  |  |  |  |  |  |  |  |  |  |  |  |  |  |

| | | | R1 | R2 | R3 | R4 | R6 | R7 | R8 | R9 | R10 | R11 | R12 | R13 | R14 | R15 | R16 | R17 | R18 | R19 | R20 | RX.. | F1 | F2 | FX.. |
|---|---|---|---|---|---|---|---|---|---|---|---|---|---|---|---|---|---|---|---|---|---|---|---|---|---|
| LFO | | | | | | | | | | | | | | | | | | | | | | | | Rules | | | FO/APR |
| F1 | | C1 | P | V | L | A | A | - | - | - | - | A | - | A | - | A | - | L | V | - | | | - | R | |
| F2 | | C2 | | | | | | | | | | | | | | | | | | | | | | O | - | |
| F3 | Conditions | C3 | L | - | A | - | L | U | - | L | - | K | - | - | L | - | U | - | - | U | | | O | O | |
| F4 | | C4 | | | | | | | | | | | | | | | | | | | | | | | - | |
| F5 | | C5 | - | V | - | - | - | P | K | - | U | - | - | - | U | - | - | - | K | P | - | | O | O | |
| F6 | | C6 | K | P | U | - | - | - | - | - | U | P | - | - | U | - | - | - | - | - | | | R | R | |
| F7 | | C7 | | | | | | | | | | | | | | | | | | | | | | | | |
| F9 | | C8 | - | L | - | - | - | - | V | U | P | - | - | - | V | K | - | L | - | | | | O | C | |
| | | C9 | | | | | | | | | | | | | | | | | | | | | | | - | |
| | | CX.. | | | | | | | | | | | | | | | | | | | | | | | | |

| | | | | | | | | | | | | | | | | | | | | | | FO | | |
|---|---|---|---|---|---|---|---|---|---|---|---|---|---|---|---|---|---|---|---|---|---|---|---|---|
| | O1 | - | - | N | - | - | - | - | - | N | - | - | Y | - | N | - | - | N | - | N | | | | |
| | O2 | - | - | - | - | - | - | - | - | - | - | - | - | - | - | Y | - | - | - | - | | F3 | | |
| | O3 | N | - | - | N | N | - | Y | - | - | Y | Y | - | N | - | N | - | N | - | - | | | | |
| | O4 | N | - | - | - | Y | Y | - | - | - | - | - | Y | - | - | - | - | - | - | - | | F5 | | |
| Principal Observations | O5 | N | - | - | N | - | - | - | - | Y | - | - | - | - | - | - | - | - | - | N | | F4 | | |
| | O6 | - | N | - | - | - | - | N | N | - | - | N | - | - | N | - | - | N | N | - | | | | |
| | O7 | - | - | - | - | - | - | - | - | - | - | - | N | - | - | Y | - | - | - | | F7 | | |
| | O8 | - | - | - | Y | - | Y | Y | - | Y | - | - | - | - | - | - | - | - | - | - | | | | |
| | O9 | N | - | - | - | - | Y | - | - | - | Y | - | N | - | - | - | - | - | - | - | | F1 | | |
| | O10 | - | Y | N | - | - | - | - | Y | - | - | - | - | - | - | - | - | - | Y | - | | | | |
| | O11 | Y | N | - | - | - | - | Y | - | - | - | - | - | - | - | - | - | - | - | - | | | | |
| | O12 | - | - | - | - | - | - | N | - | - | Y | N | - | - | - | - | Y | - | - | - | | F6 | | |
| | O13 | N | - | - | Y | - | N | N | - | - | - | - | - | - | - | - | - | Y | - | - | | | | |
| | O14 | - | - | - | - | - | Y | - | - | - | - | - | N | - | - | - | - | - | - | - | | | | |
| | O15 | N | - | Y | - | Y | N | - | Y | - | Y | - | Y | - | Y | - | Y | - | Y | - | | F2 | | |
| | O16 | - | - | - | N | Y | - | - | - | Y | Y | - | Y | N | Y | - | - | - | - | - | | | | |
| | OX | | | | | | | | | | | | | | | | | | | | | | | | |

B2

FIG. 7 condt.

C1

| LFO |
|-----|
| F1 |
| F2 |
| F3 |
| F4 |
| F5 |
| F6 |
| F7 |
| F9 |

|  |  | Rules | | | | | | | | | | | | | | | | | | | | FO/APR |
|--|--|--|--|--|--|--|--|--|--|--|--|--|--|--|--|--|--|--|--|--|--|--|
|  |  | R1 | R2 | R3 | R4 | R6 | R7 | R8 | R9 | R10 | R11 | R12 | R13 | R14 | R15 | R16 | R17 | R18 | R19 | R20 | RX.. | F2 |
| Conditions | C1 | P | V | L | A | A | - | - | - | - | A |   |    | A | - | A | - | L | V | - |  | R |
|  | C3 | L | - | A | - | L | U | - | L | - | K | - |    | - | L | - | U | - | - | U |  | O |
|  | C5 | - | V | - | - | - | P | K | - | U | - | - |    | U | - | - | - | K | P | - |  | O |
|  | C6 | K | P | U | - | - | - | - | - | U | P |   |    | - | U | - | - | - | - | - |  | R |
|  | C8 | - | L | - | - | - | - | V | U | P | - |   |    | - | - | V | K | - | L | - |  | C |
|  | CX.. |   |   |   |   |   |   |   |   |   |   |   |    |   |   |   |   |   |   |   |  |   |
|  |  |  |  |  |  |  |  |  |  |  |  |  |  |  |  |  |  |  |  |  |  | FO |
| Principal Observations | O1 | - | - | N | - | - | - | - | - | N | - | - |    | - | N | - | - | N | - | N |  |  |
|  | O2 | - | - | - | - | - | - | - | - | - | - | - |    | - | - | Y | - | - | - | - |  | F3 |
|  | O3 | N | - | - | N | N | - | Y | - | - | Y | Y |    | N | - | N | - | N | - | - |  |  |
|  | O4 | N | - | - | - | Y | Y | - | - | - | - | - |    | - | - | - | - | - | - | - |  | F5 |
|  | O5 | N | - | - | N | - | - | - | - | Y | - | - |    | - | - | - | - | - | - | N |  | F4 |
|  | O6 | - | N | - | - | - | - | N | N | - | - | N |    | - | N | - | - | N | N | - |  |  |
|  | O7 | - | - | - | - | - | - | - | - | - | - | - |    | N | - | - | Y | - | - | - |  | F7 |
|  | O8 | - | - | - | Y | - | Y | Y | - | Y | - | - |    | - | - | - | - | - | - | - |  |  |
|  | O9 | N | - | - | - | - | Y | - | - | - | Y | - |    | - | - | - | - | - | - | - |  | F1 |
|  | O10 | - | Y | N | - | - | - | - | Y | - | - | - |    | - | - | - | - | - | Y | - |  |  |
|  | O11 | Y | N | - | - | - | - | Y | - | - | - | - |    | - | - | - | - | - | - | - |  |  |
|  | O12 | - | - | - | - | - | N | - | - | Y | N | - |    | - | - | Y | - | - | - | - |  | F6 |
|  | O13 | N | - | - | Y | - | N | N | - | - | - | - |    | - | - | - | Y | - | - | - |  |  |
|  | O14 | - | - | - | - | - | Y | - | - | - | - | - |    | - | - | - | - | - | - | - |  |  |
|  | O15 | N | - | Y | - | Y | N | - | Y | - | Y | - |    | - | Y | - | Y | - | Y | - |  | F2 |
|  | O16 | - | - | - | N | Y | - | - | Y | Y | - |   |    | N | Y | - | - | - | - | - |  |  |
|  | OX |   |   |   |   |   |   |   |   |   |   |   |    |   |   |   |   |   |   |   |  |   |

C2

FIG. 7 condt.

D1

| LFO |
|-----|
| F1 |
| F2 |
| F3 |
| F4 |
| F5 |
| F6 |
| F7 |
| F9 |

| | | Rules | | | | | | | | | | | | | | | | | | FO/APR |
|---|---|---|---|---|---|---|---|---|---|---|---|---|---|---|---|---|---|---|---|---|
| | | R1 | R2 | R3 | R4 | R6 | R7 | R8 | R9 | R10 | R11 | R12 | R14 | R15 | R16 | R17 | R18 | R19 | R20 | RX.. | F2 |
| Conditions | C1 | P | V | L | A | A | - | - | - | - | - | A | A | - | A | - | L | V | - | | R |
| | C3 | L | - | A | - | L | U | - | L | - | K | - | - | L | - | U | - | - | U | | O |
| | C5 | - | V | - | - | - | P | K | - | U | - | - | U | - | - | - | K | P | - | | O |
| | C6 | K | P | U | - | - | - | - | - | - | U | P | - | U | - | - | - | - | - | | R |
| | C8 | - | L | - | - | - | - | V | U | P | - | - | - | V | K | - | L | - | - | | C |
| | CX.. | | | | | | | | | | | | | | | | | | | | |
| | | | | | | | | | | | | | | | | | | | | | FO |
| Principal Observations | O1 | - | - | N | - | - | - | - | - | N | - | - | - | N | - | - | N | - | N | | |
| | O2 | - | - | - | - | - | - | - | - | - | - | - | - | - | Y | - | - | - | - | | F3 |
| | O3 | N | - | - | N | N | - | Y | - | - | Y | Y | N | - | N | - | N | - | - | | |
| | O4 | N | - | - | - | Y | Y | - | - | - | - | - | - | - | - | - | - | - | - | | F5 |
| | O5 | N | - | - | N | - | - | - | - | Y | - | - | - | - | - | - | - | - | N | | F4 |
| | O6 | - | N | - | - | - | - | N | N | - | Y | - | N | - | - | N | N | - | - | | |
| | O7 | - | - | - | - | - | - | - | - | - | - | N | - | - | Y | - | - | - | - | | F7 |
| | O8 | - | - | - | Y | - | Y | Y | - | Y | - | - | - | - | - | - | - | - | - | | |
| | O9 | N | - | - | - | - | Y | - | - | Y | - | - | - | - | - | - | - | - | - | | F1 |
| | O10 | - | Y | N | - | - | - | Y | - | - | - | - | - | - | - | - | - | Y | - | | |
| | O11 | Y | N | - | - | - | Y | - | - | - | - | - | - | - | - | - | - | - | - | | |
| | O12 | - | - | - | - | - | N | - | - | Y | N | - | - | - | Y | - | - | - | - | | F6 |
| | O13 | N | - | - | Y | - | N | N | - | - | - | - | - | - | Y | - | - | - | - | | |
| | O14 | - | - | - | - | - | Y | - | - | - | - | - | - | - | - | - | - | - | - | | |
| | O15 | N | - | Y | - | Y | N | - | Y | - | Y | - | - | Y | - | Y | - | Y | - | | F2 |
| | O16 | - | - | - | N | Y | - | - | - | Y | Y | - | N | Y | - | - | - | - | - | | |
| | OX | | | | | | | | | | | | | | | | | | | | |

D2

FIG. 7 condt.

| LFO |
|---|
| F1 |
| F2 |
| F3 |
| F4 |
| F5 |
| F6 |
| F7 |
| F9 |

| | | R1 | R2 | R3 | R4 | R6 | R7 | R8 | R9 | R10 | R11 | R12 | R14 | R15 | R16 | R17 | R18 | R19 | R20 | RX.. | FO/APR |
|---|---|---|---|---|---|---|---|---|---|---|---|---|---|---|---|---|---|---|---|---|---|
| | | | | | | | | | | | | | | | | | | | | | F2 |
| Conditions | C1 | P | V | L | A | A | | | - | | | A | | - | A | | - | L | V | | R |
| | C3 | L | | A | | L | U | | L | | K | | | L | | U | | - | U | | O |
| | C5 | | V | | - | P | K | | U | | - | U | | - | | | K | P | | | O |
| | C6 | K | P | U | | - | | | U | P | | U | | | | | - | | | | R |
| | C8 | | - | | - | | V | U | P | | | | V | | V | K | | L | | | C |
| | CX.. | | | | | | | | | | | | | | | | | | | | |
| | | | | | | | | | | | | | | | | | | | | | |
| | | | | | | | | | | | | | | | | | | | | | FO |
| Principal Observations | O1 | | N | | - | | N | | - | | | N | | | N | | - | N | | | F2 |
| | O2 | | - | | | | - | | | | | - | | - | | | | | | | F3 |
| | O3 | N | - | N | N | Y | - | | Y | | Y | N | | N | - | | N | - | | | F5 |
| | O4 | N | - | | Y | Y | | | - | | | | | | | | - | | | | F4 |
| | O5 | N | - | N | - | | - | Y | - | | | | | | | | - | N | | | |
| | O6 | | N | - | | - | N | N | - | | N | | | N | | - | N | N | | | F7 |
| | O7 | | - | | - | | - | | | | N | | | - | Y | | - | | | | F1 |
| | O8 | | - | Y | | Y | | | Y | | | | | | | | - | | | | |
| | O9 | N | - | | N | - | | | Y | | | | | | - | | - | | | | F6 |
| | O10 | Y | N | - | | Y | | | - | | | | | | - | | Y | | | | |
| | O11 | Y | N | - | | | Y | | | | | | | | | | | | | | |
| | O12 | Y | - | | N | - | | Y | N | | - | Y | | - | | | | | | | |
| | O13 | N | | Y | - | N | N | | - | | | - | | - | | Y | - | | | | |
| | O14 | | | | | | | | | | | | | | | | | | | | |
| | O15 | N | - | Y | - | Y | N | - | Y | - | Y | - | - | Y | - | Y | - | Y | - | | F2 |
| | O16 | | | N | Y | | Y | | Y | | | N | Y | | Y | | - | | | | |
| | OX | | | | | | | | | | | | | | | | | | | | |

| | | Rules | | | | | | | FO/APR |
|---|---|---|---|---|---|---|---|---|---|
| | | R3 | R6 | R9 | R11 | R15 | R17 | R19 | RX.. | F2 |
| Conditions | C1 | L | A | - | - | - | - | V | | R |
| | C3 | A | L | L | K | L | U | - | | O |
| | C5 | - | - | - | - | - | - | P | | O |
| | C6 | U | - | - | U | U | - | - | | R |
| | C8 | - | - | V | P | - | K | L | | C |
| | CX.. | | | | | | | | | |
| | | | | | | | | | | FO |
| Principal Observations | O1 | N | - | - | - | N | - | - | | |
| | O2 | ▨ | ▨ | ▨ | ▨ | ▨ | ▨ | ▨ | ▨ | F3 |
| | O3 | - | N | - | Y | - | - | - | | |
| | O4 | - | Y | - | - | - | - | - | | F5 |
| | O5 | ▨ | ▨ | ▨ | ▨ | ▨ | ▨ | ▨ | ▨ | F4 |
| | O6 | - | - | N | - | N | - | N | | |
| | O7 | - | - | - | - | - | Y | - | | F7 |
| | O8 | ▨ | ▨ | ▨ | ▨ | ▨ | ▨ | ▨ | ▨ | |
| | O9 | - | - | - | Y | - | - | - | | F1 |
| | O10 | N | - | Y | - | - | - | Y | | |
| | O11 | ▨ | ▨ | ▨ | ▨ | ▨ | ▨ | ▨ | ▨ | |
| | O12 | - | - | - | Y | - | Y | - | | F6 |
| | O13 | ▨ | ▨ | ▨ | ▨ | ▨ | ▨ | ▨ | ▨ | |
| | O14 | - | - | - | - | - | - | - | | |
| | O15 | Y | Y | Y | Y | Y | Y | Y | | F2 |
| | O16 | - | Y | - | N | Y | - | - | | |
| | OX | | | | | | | | | |

C2

| | | Rules | | | | | | | FO/APR |
|---|---|---|---|---|---|---|---|---|---|
| | | R3 | R6 | R9 | R11 | R15 | R17 | R19 | RX.. | F2 |
| Conditions | C1 | L | A | - | - | - | - | V | | R |
| | C3 | A | L | L | K | L | U | - | | O |
| | C5 | - | - | - | - | - | - | P | | O |
| | C6 | U | - | - | U | U | - | - | | R |
| | C8 | - | - | V | P | - | K | L | | C |
| | CX.. | | | | | | | | | |
| | | | | | | | | | | FO |
| Principal Observations | O1 | N | - | - | - | N | - | - | | |
| | O3 | - | N | - | Y | - | - | - | | |
| | O4 | - | Y | - | - | - | - | - | | F5 |
| | O6 | - | - | N | - | N | - | N | | |
| | O7 | - | - | - | - | - | Y | - | | F7 |
| | O9 | - | - | - | Y | - | - | - | | F1 |
| | O10 | N | - | Y | - | - | - | Y | | |
| | O12 | - | - | - | Y | - | Y | - | | F6 |
| | O14 | - | - | - | - | - | - | - | | |
| | O15 | Y | Y | Y | Y | Y | Y | Y | | F2 |
| | O16 | - | Y | - | N | Y | - | - | | |
| | OX | | | | | | | | | |

FIG. 9 condt.

FIG. 10

A1 (LOQ): O1, O3, O4, O6, O9, O10, O12, O14, O15, O16 Y

A2:

Conditions:

|    | R3 | R6 | R9 | R11 | R15 | R17 | R19 |
|----|----|----|----|----|-----|-----|-----|
| C1 | L  | A  | -  | -  | -   | -   | V   |
| C3 | A  | L  | L  | K  | L   | U   | -   |
| C5 | -  | -  | -  | -  | -   | -   | P   |
| C6 | U  | -  | -  | U  | U   | -   | -   |
| C8 | -  | -  | V  | P  | -   | K   | L   |

Principal Observations:

|     | R3 | R6 | R9 | R11 | R15 | R17 | R19 |
|-----|----|----|----|----|-----|-----|-----|
| O1  | N  | -  | -  | -  | N   | -   | -   |
| O3  | -  | N  | -  | Y  | -   | -   | -   |
| O4  | -  | Y  | -  | -  | -   | -   | -   |
| O6  | -  | -  | N  | -  | N   | -   | N   |
| O9  | -  | -  | -  | Y  | -   | -   | -   |
| O10 | N  | -  | Y  | -  | -   | -   | Y   |
| O12 | -  | -  | -  | Y  | -   | Y   | -   |
| O14 | -  | -  | -  | -  | -   | -   | -   |
| O15 | -  | -  | -  | -  | -   | Y   | -   |
| O16 | -  | Y  | -  | N  | Y   | Y   | -   |
| OX  |    |    |    |    |     |     |     |

A3 (LOC):

| C   | APR |
|-----|-----|
| C8  | C   |
| C3  | O   |
| C5  | O   |
| C1  | R   |
| C6  | R   |
| CX… |     |

---

B1 (LOQ): O1, O3, O4, O6, O9, O10, O12, O14, O15 Y

B2:

Conditions:

|    | R3 | R6 | R9 | R11 | R15 | R17 | R19 |
|----|----|----|----|----|-----|-----|-----|
| C1 | L  | A  | -  | -  | -   | -   | V   |
| C3 | A  | L  | L  | K  | L   | U   | -   |
| C5 | -  | -  | -  | -  | -   | -   | P   |
| C6 | U  | -  | -  | U  | U   | -   | -   |
| C8 | -  | -  | V  | P  | -   | K   | L   |

Principal Observations:

|     | R3 | R6 | R9 | R11 | R15 | R17 | R19 |
|-----|----|----|----|----|-----|-----|-----|
| O1  | N  | -  | -  | -  | N   | -   | -   |
| O3  | -  | N  | -  | Y  | -   | -   | -   |
| O4  | -  | Y  | -  | -  | -   | -   | -   |
| O6  | -  | -  | N  | -  | N   | -   | N   |
| O9  | -  | -  | -  | Y  | -   | -   | -   |
| O10 | N  | -  | Y  | -  | -   | -   | Y   |
| O12 | -  | -  | -  | Y  | -   | Y   | -   |
| O14 | -  | -  | -  | -  | -   | -   | -   |
| O15 | -  | -  | Y  | -  | -   | Y   | -   |
| O16 | -  | Y  | -  | N  | Y   | Y   | -   |
| OX  |    |    |    |    |     |     |     |

B3 (LOC):

| C   | APR |
|-----|-----|
| C8  | C   |
| C3  | O   |
| C5  | O   |
| C1  | R   |
| C6  | R   |
| CX… |     |

FIG. 10 condt.

FIG. 10 condt.

E1, E2, E3, F1, F2, F3 (diagrams)

| LOQ | | | | | | | | |
|---|---|---|---|---|---|---|---|---|
| | | R3 | R6 | R9 | R11 | R15 | R17 | R19 |
| Conditions | C1 | L | A | - | - | - | - | V |
| | C3 | A | L | L | K | L | U | - |
| | C5 | - | - | - | - | - | - | P |
| | C6 | U | - | - | U | U | - | - |
| | C8 | - | - | V | P | - | K | L |
| Principal Observations | O1 | N | - | - | - | N | - | - |
| | O3 | - | N | - | Y | - | - | - |
| | O4 | - | Y | - | - | - | - | - |
| | O6 | - | - | N | - | N | - | N |
| | O9 | - | - | - | Y | - | - | - |
| | O10 | N | - | Y | - | - | - | Y |
| | O12 | - | - | - | Y | - | Y | - |
| | O14 | - | - | - | - | - | - | - |
| | O15 | - | - | Y | - | - | Y | - |
| | O16 | - | Y | - | N | Y | Y | - |
| | OX | | | | | | | |

G1 (left label), G2 (bottom label), G3 (right label)

| LOC | |
|---|---|
| C | Lih |
| C1 | A |
| C8 | K |
| C3 | U |
| C6 | R |
| C5 | O |

FIG. 10 condt.

A

| | | | | | | | | | | | Flag (status) |
|---|---|---|---|---|---|---|---|---|---|---|---|
| Conditions | C20 | L | A | - | - | K | - | - | P | - | A | |
| | C21 | A | L | L | K | - | L | U | - | - | | |
| | C22 | - | - | - | - | - | - | - | P | - | | |
| | C23 | U | - | - | U | - | - | - | - | - | | |
| | C23 | - | - | V | P | - | - | K | - | - | | |
| | | | | | | | | | | | | |
| Principal Observations | O21 | Y | - | - | - | Y | N | - | - | - | - | Fg1 (Y) |
| | O22 | - | - | - | - | - | - | - | - | - | N | Fg1 (Y) |
| | O23 | - | Y | - | - | Y | - | - | Y | - | - | Fg1 (Y) |
| | O24 | - | - | N | - | - | N | - | - | - | - | Fg1 (Y) |
| | O25 | - | - | - | - | - | - | - | - | - | Y | Fg3 (Y) |
| | O26 | N | - | Y | - | - | - | - | - | - | - | Fg3 (N) |
| | O27 | - | - | - | Y | - | - | Y | - | - | - | Fg4 (Y) |
| | O28 | - | - | - | - | - | N | - | - | - | - | Fg5 (black) |
| | O29 | - | - | - | - | - | - | - | - | Y | - | Fg5 (white) |

Fg 1 (Y) identified

B

| | | | | | | | | | | | Flag (status) |
|---|---|---|---|---|---|---|---|---|---|---|---|
| 10 { Conditions | C20 | L | A | - | - | K | - | - | P | A | | |
| | C21 | A | L | L | K | - | L | U | - | - | | |
| | C22 | - | - | - | - | - | - | - | - | | | |
| | C23 | U | - | - | U | - | - | - | - | | | |
| | C23 | - | - | V | P | - | - | K | - | | | |
| | | | | | | | | | | | | |
| 20 { Principal Observations | O21 | Y | - | - | - | Y | N | - | - | - | Fg1 (Y) |
| | O22 | - | - | - | - | - | - | - | - | N | Fg1 (Y) |
| | O23 | - | Y | - | - | Y | - | - | Y | - | Fg1 (Y) |
| | O24 | - | - | N | - | - | N | - | - | - | Fg1 (Y) |

METHOD AND SYSTEM FOR ASSISTING DETERMINATION OF A MEDICAL CONDITION

This application is the U.S. national phase of International Application No. PCT/EP2015/054059 filed 26 Feb. 2015 which designated the U.S. and claims priority to International Application No. PCT/EP2014/053741 filed 26 Feb. 2014, the entire contents of each of which are hereby incorporated by reference.

FIELD OF THE INVENTION

The present invention is in the field of methods and systems for assisting a diagnosis based on medical imaging data.

BACKGROUND TO THE INVENTION

A clinician is required to make a clinical judgments based on the content of a bodily medical image. Current diagnostic support systems are mostly limited to encyclopedia-like online databases of diseases possibly associated with specific imaging features, and imaging features associated with certain diseases. These databases give useful general information, but do not provide a tailored solution for a diagnostic problem in a specific patient. Even an experienced clinician cannot alone make a diagnosis where there are difficult cases of radiology interpretation; expertise in recognising an abnormality in radiological pattern particular to one organ, cannot be transferred to other organs or regions of the body in view that each organ or bodily region will present a different radiological pattern.

One specific abnormality/observation does not necessarily correspond to one possible diagnosis, even if the observation is refined using specific combinations of findings. In fact, one single type of abnormality may correspond to many different diseases. Moreover, one single abnormality may show different imaging features on different types of images.

A hepatic lesion may be seen on MRI. The lesion may be hypointense on T1-weighted images (1), hyperintense on T2-weighted images (2), hyperintense on DWI images (3), invisible on T1-weighted images out of phase (4), hyperintense on arterial-phase images (5), isointense on portal venous phase images (6), hypointense on images in the equilibrium phase (7), and hyperintense on images in the hepatobiliary phase (8). Moreover, ultrasonography may reveal that the lesion was hyperechoic (9). Moreover, the lesion may be heterogeneous (10), well-defined (11), and may contain a calcification (12). Moreover, there may be another similar lesion in the liver (13) and an abnormality in the spleen (14). The patient may be a male (15) with African roots (16) who has fever (17) and leucocytosis (18), and antecedents of prostate cancer (19) and hepatitis (20). In such typical example there are over 20 different indicators to be reconciled by the clinician. The correct diagnoses must be reached, and also cost-effectively. A conventional diagnostic system would not provide an accurate result because the specific diagnostic value of the different abnormalities has to be taken into account. For instance, feeding a system with the information that a lesion is "hypointense on T1-weighted MRI" has no value because >90% of diseases may have that appearance. A critical factor determining clinical acceptance is also the time needed to resolve a case. Radiologists (and clinicians in general) are under time constraints; any diagnostic support system or expert system leading to significant time loss or workflow interruption will not be used. Difficulties in building and maintaining such systems, and lack of acceptance by users have resulted in slow introduction in clinical practice.

The present invention provides a methodological solution to create a system that allows the clinician to reach a diagnosis in a minimum number of steps, and at the same time being accurate.

SOME EMBODIMENTS OF THE INVENTION

The present invention relates to a method for assisting a user in determining a medical condition in a subject from one or more medical images, the method comprising the steps:
i) outputting from a database (FIG. 7, A2) a list of foundation observations (FIG. 7, A1), LFO, corresponding to a set of foundation observations, SFO, which SFO is a predefined subset of a multitude of observations, MO, each observation in the MO corresponding to a description of a medical-image- or subject-related observation,
ii) receiving an input (FIG. 7, B1) of a selection of at least one foundation observation from the LFO,
iii) generating:
    a set of conditions SC linked to the selected FO in the database (FIG. 7 B2),
    a set of rules, SR, linked to the selected FO in the database (FIG. 9 A2), and
    from the MO a set of observations, SO, linked the SR in the database (FIG. 9 B2),
iv) generating and outputting a list of conditions LOC from the SC (FIG. 10 A3) and a list of questions LOQ from the SO (FIG. 10 A1),
v) receiving an input (FIG. 10 A1) as to the status of one question in the LOQ, whereby the status is an indication of the presence, absence or unknown status in regard of the subject,
vi) updating and outputting:
    the LOC (FIG. 10 B3, C3, D3, E3, F3), wherein likelihood(s) for condition(s) linked to the rules satisfied by status received in step (v) are provided, and
    the LOQ (FIG. 10 B1, C1, D1, E1, F1), wherein at least the question corresponding to the observation status received in step (v) is removed,
vii) repeating steps v) to vi) optionally until there are no more questions in the LOQ (FIG. 10 G1).

The present invention further relates to a method for assisting a user in determining a medical condition in a subject from one or more medical images, the method comprising the steps:
i) outputting to the user a list of foundation observations (FIG. 7 A1), LFO, from a database (FIG. 7 A2), wherein the database contains:
    a multitude of observations, MO, each corresponding to a description of a medical-image- or subject-related observation,
    a set of foundation observations, SFO, corresponding to a predefined subset of the MO, and used to generate the LFO,
    a multitude of conditions, MC, each linked to at least one foundation observation,
    a multitude of rules, MR,
        wherein each rule in the MR links a discrete likelihood of at least one condition with the absence or presence of at least one observation, ii) receiving an input (FIG. 7 B1) of a selection of at least one FO from the LFO, iii) generating:
   a set of conditions, SC, from the MC, wherein conditions not linked to the selected FO are excluded (FIG. 7 B2),
   a set of rules, SR, from the MR, wherein rules that are not linked to the presence of the selected FO are excluded (FIG. 9 A2),
   a set of observations, SO, from the MO, wherein observations not linked to rules present in the SR are excluded (FIG. 9 B2), iv) generating and outputting a list of conditions LOC from the SC (FIG. 10 A3), and a list of questions, LOQ from the SO (FIG. 10 A1), v) receiving an input (FIG. 10 A1) as to the status of one question in the LOQ whereby the status is an indication of the presence, absence or unknown status in regard of the subject, vi) updating and outputting:
   the LOC (FIG. 10 B3, C3, D3, E3, F3), wherein likelihood(s) for condition(s) linked to the rules satisfied by status received in step (v) are provided, and
   the LOQ (FIG. 10 B1, C1, D1, E1, F1), wherein at least the question corresponding to the observation status received in step (v) is removed, vii) repeating steps v) to vi) optionally until there are no more questions in the LOQ (FIG. 10 G1).

A plurality of conditions in the SC may be linked to a plurality of foundation observations in the SO by discrete a priori ratings, APRs, wherein each foundation observation is linked to the corresponding condition by one APR (FIG. 7 A2).

The number of categories of discrete a priori ratings may be between 3 and 5, preferably 3.

Each condition in the LOC in step iv) may be initially assigned the corresponding a priori rating according to the at least one FO selected from the LFO in step ii) and the links between the plurality of conditions in the SC and plurality of foundation observations in the SFO above (FIG. 10 A3), and the likelihood(s) for condition(s) provided in step vi) replace the a priori rating initially assigned to the same condition (FIG. 10 D3, E3, F3).

A satisfied rule may indicate one or more specified conditions each at a specified likelihood on the one hand, and a specified absence or presence of one or more specified observations on the other hand.

The conditions in the LOC are ordered according to likelihood, optionally during the updating.

The observations in SFO may be pre-defined patterns in the one or more medical images.

The number of discrete likelihoods may be between 4 and 8, preferably 6.

Two or more observations in the SPO may constitute a subset of observations, SSO, such that the presence or absence of one observation of the SSO is indicative of the presence or absence of the remaining observations in the SSO.

The revised LOQ in step vi) may be devoid of all questions enquiring as to the status of the observations in the SSPO, when the answer received in step ii) is an indication of the status of one observation of the SSPO.

Two or more observations in the SPO may constitute a linked set of observations, LSO, associated to a status of a linking observation, which LSO is used to generate a corresponding linked set of questions LSOQ enquiring as to the status of the LSO, such that an indication of a status of the linking observation initiates outputting the LSOQ enquiring as to the status observations of the LSPO.

Step ii) may further comprise the step of presenting the user with a series of choices, arranged in increasing specificity, to guide the user towards a selection of an indication of the FO present in the patient.

The LOQ in step iv) may exclude those which lead to populating the LOC with conditions having the lowest likelihoods.

The medical image-related observations may comprise the recognition of a morphological pattern from a medical image and/or the patient-related observations may comprise age, gender, symptoms, medical history, laboratory results, or a combination thereof.

The status of some of the observations in the SPO are determined using information from another database, preferably from a picture archive and communication system (PACS), radiology information system (RIS) and/or hospital imaging system (HIS), the remaining observations in the SPO being reformulated as questions to the user that initially populate LOQ.

Another aspect of the present invention relates to a method for assisting a user in determining a medical condition in a subject from one or more medical images, the method comprising the steps:

i) outputting to the user a list of questions, LOQ, from a database, each enquiring as to the status of a principal observation in the subject pertinent to the one or more medical images, whereby the status comprises an indication of the presence, absence, or lack of knowledge of the observation in the subject, and
   whereby the database comprises:
   a set of principal observations, SPO used to generate the LOQ;
   a set of conditions, SC, used to generate a list of conditions, LOC;
   wherein each condition in the SC is assigned one or more rules, linking a discrete likelihood of the condition with the absence or presence of at least one of the principal observations in the SPO;

ii) receiving from the user an indication of the status of one principal observation in the LOQ;

iii) updating the LOC and associated likelihoods to satisfy the user-indicated status of the principal observation of step ii) according to the one or more rules, iv) outputting to the user, at least part of the list of conditions, LOC and associated discrete likelihood updated in step iii);

v) outputting to the user a revised LOQ, wherein at least the question corresponding to observation status received in step ii) is removed; and vi) repeating steps ii) to v), optionally until there are no more questions in the LOQ, thereby arriving at the LOC and discrete likelihoods that satisfy the status of the observations according to the one of more rules.

The SPO in the database may be medical image-related observations and/or patient-related observations. The number of discrete likelihoods may be between 4 and 8, preferably 6. Two or more principal observations in the SPO may constitute a subset of principal observations, SSPO, such that the presence or absence of one observation of the SSPO is indicative of the presence or absence of the remaining observations in the SSPO. The revised LOQ in step v) may be devoid of all questions enquiring as to the status of the observations in the SSPO, when the answer received in step ii) is an indication of the status of one observation of the SSPO. Two or more principal observations in the SPO may constitute a linked set of principal observations, LSPO, associated to a status of a linking principal observation, which LSPO is used to generate a corresponding linked set of questions LSOQ enquiring as to the status of the LSPO, such that an indication of a status of the linking principal observation initiates outputting the LSOQ enquiring as to the status observations of the LSPO. A condition and optionally a principal observation in the database may be associated with at least one foundation observation that is preferably a predefined pattern in the one or more medical images, which method further comprises the steps prior to step i):

a) receiving an indication of the presence of a foundation observation in the patient from a set of foundation observations, SFO, containing one or more foundation observations, and b) populating the SC in the database with conditions associated with the indicated foundation observation, and c) populating the SPO in the database with principal observations associated with the conditions in the SC populated in step b) according to the assigned rules, and optionally wherein the principal observations are associated with the indicated foundation observation.

Step a) may further comprise the step of presenting the user with a series of choices, arranged in increasing specificity, to guide the user towards a selection of an indication of the foundation observation present in the patient. The condition in the database may be associated with a location, that is a bodily location of the one or more medical images, and the method may further comprise the steps:

receiving an indication of the location of the one or more medical images in the patient from a pre-defined list containing one or more locations, and populating the SFO with foundation observations associated with the indicated location.

A principal observation and/or condition in the database may be associated with one or more flags, and method further comprise the steps prior to step i):

receiving an indication the status of one or more flags from a pre-defined list containing one or more flags, and populating the SPO and SC in the database with principal observations and/or conditions associated with the indicated flag and its status.

The flag may relate to a specific status of a condition of the patient, or to the imaging technique(s) used to acquire the one or more medical images.

The LOQ in step v) may exclude those which lead to populating the LOC with conditions having the lowest likelihoods. The medical image-related observations may comprise the recognition of a morphological pattern from a medical image and/or the patient-related observations may comprise age, gender, symptoms, medical history, laboratory results, or a combination thereof. The status of some of the principal observations in the SPO may be determined using information from another database, preferably from a picture archive and communication system (PACS), radiology information system (RIS) and/or hospital imaging system (HIS), the remaining observations in the SPO being reformulated as questions to the user that initially populate LOQ.

The present invention further relates to a computer program, or a computer program product directly loadable into the internal memory of a computer, or a computer program product stored on a computer readable medium, or a combination of such computer programs or computer program products, configured for performing one of the methods as described above.

LEGENDS TO THE FIGURES

FIG. 1 depicts a possible database structure of principal observations, conditions, associated likelihoods and observation statuses.

FIG. 2 depicts the database structure of FIG. 1 for a single condition (C1).

FIG. 7 (A1 to D2) depicts another possible database structure containing a multitude of conditions, principal observations, rules, and associated foundation observations and a priori ratings (APR). In B1, foundation observation F2 is selected, leading to the exclusion of a number of conditions and generating a priori ratings (B2). In C2, R13 is indicated as having no conditions relating thereto, the generated set of conditions and a priori ratings are depicted in D2.

Figure 8:
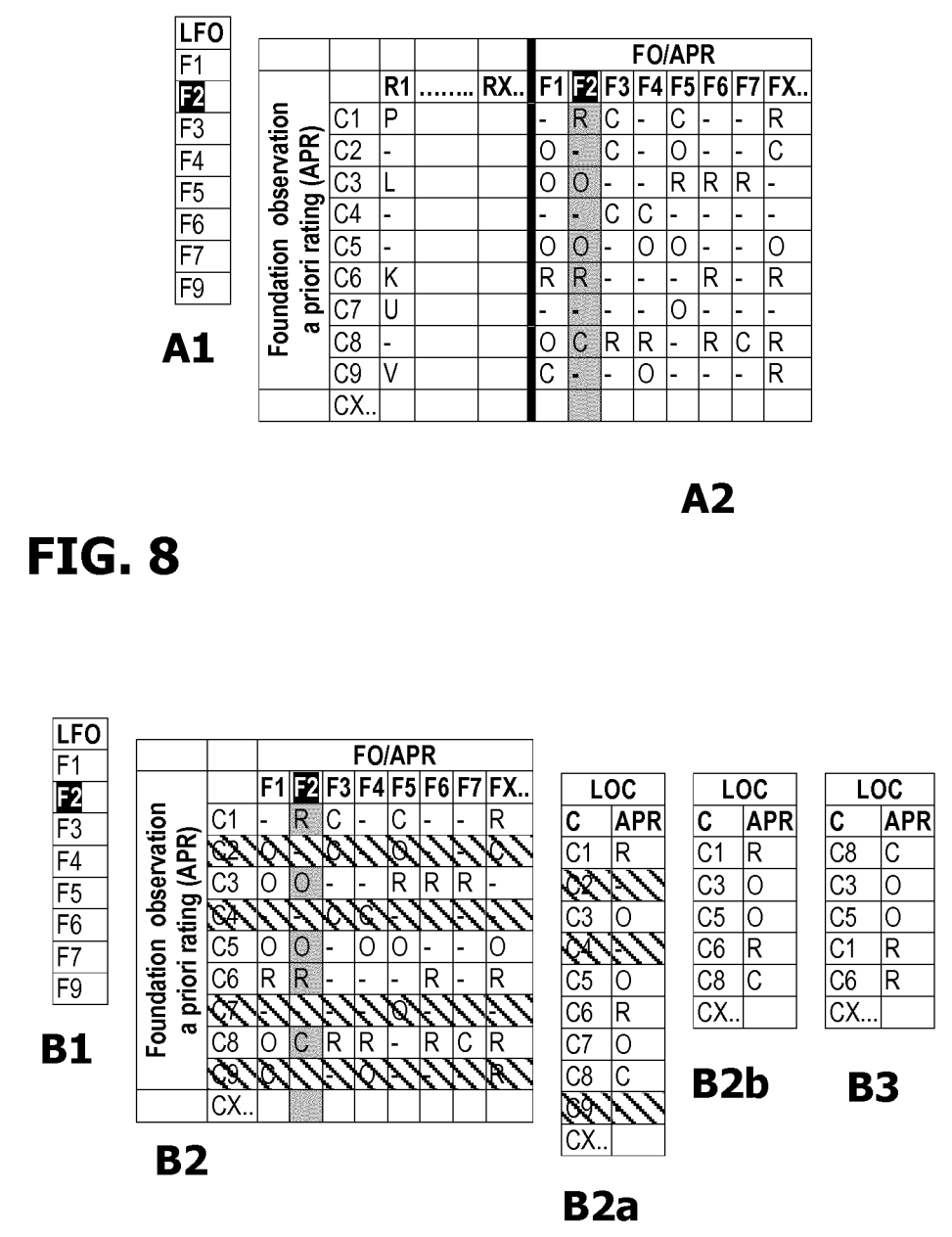

FIG. 8 (A1 to B3) depicts in more detail an association between foundation observations and conditions. In B1, foundation observation F2 is selected, leading to the exclusion of conditions not containing an a priori rating (A2 cf B2). In B2a and B2b the LOC is generated containing remaining conditions and a priori ratings wherein the list is ordered in B3.

FIG. 9 (A1 to C2) depicts the same database of FIG. 7A2. In A1, foundation observation F2 is selected that corresponds to principal observation O15, leading to the exclusion of a number of rules that are not linked to the presence of O15. The result is the excluded rules in shown in B2. Principal observations no longer linked to a rules are highlighted in B2, and excluded in C2.

Figure 10:
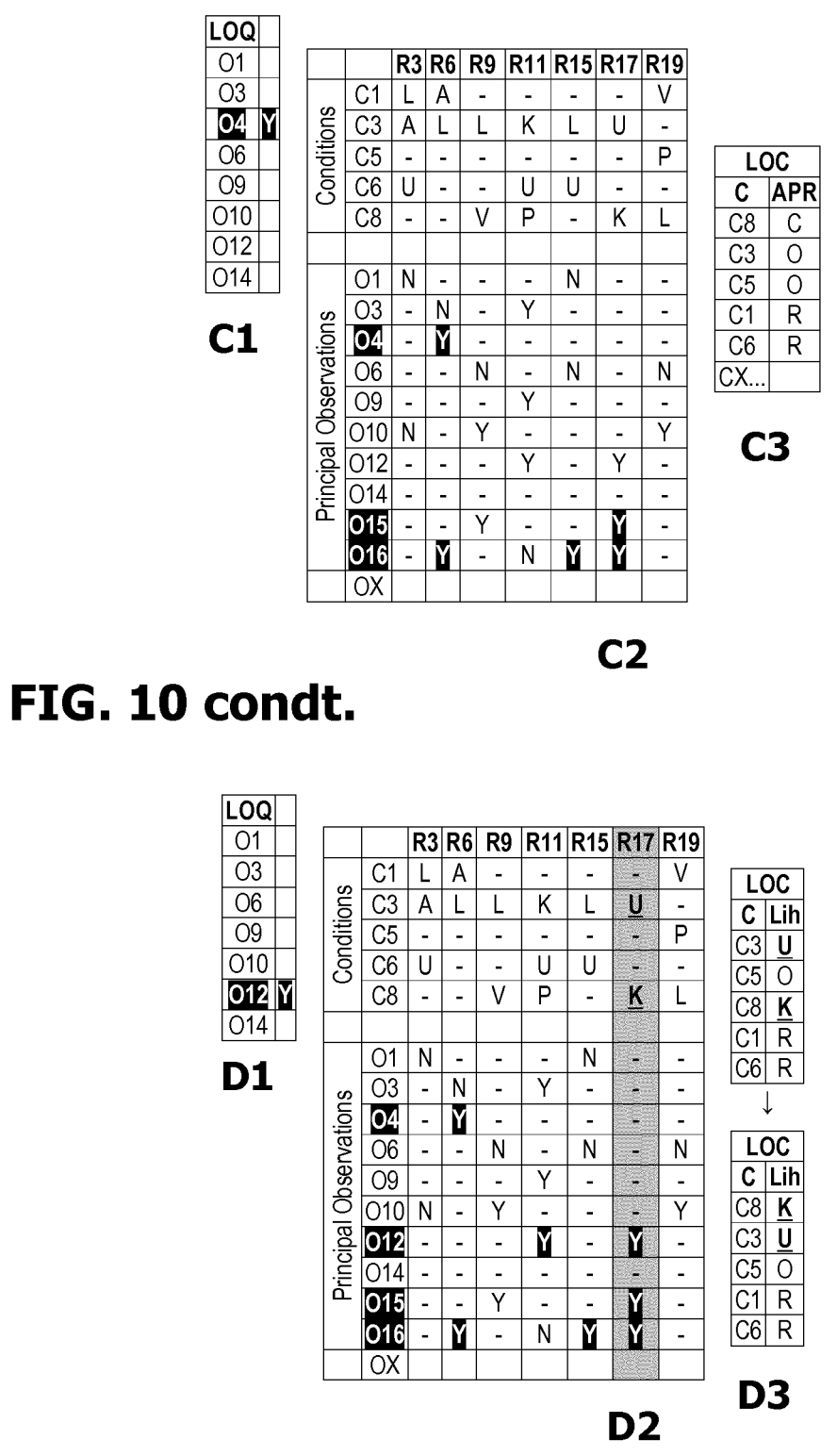
Figure 10:
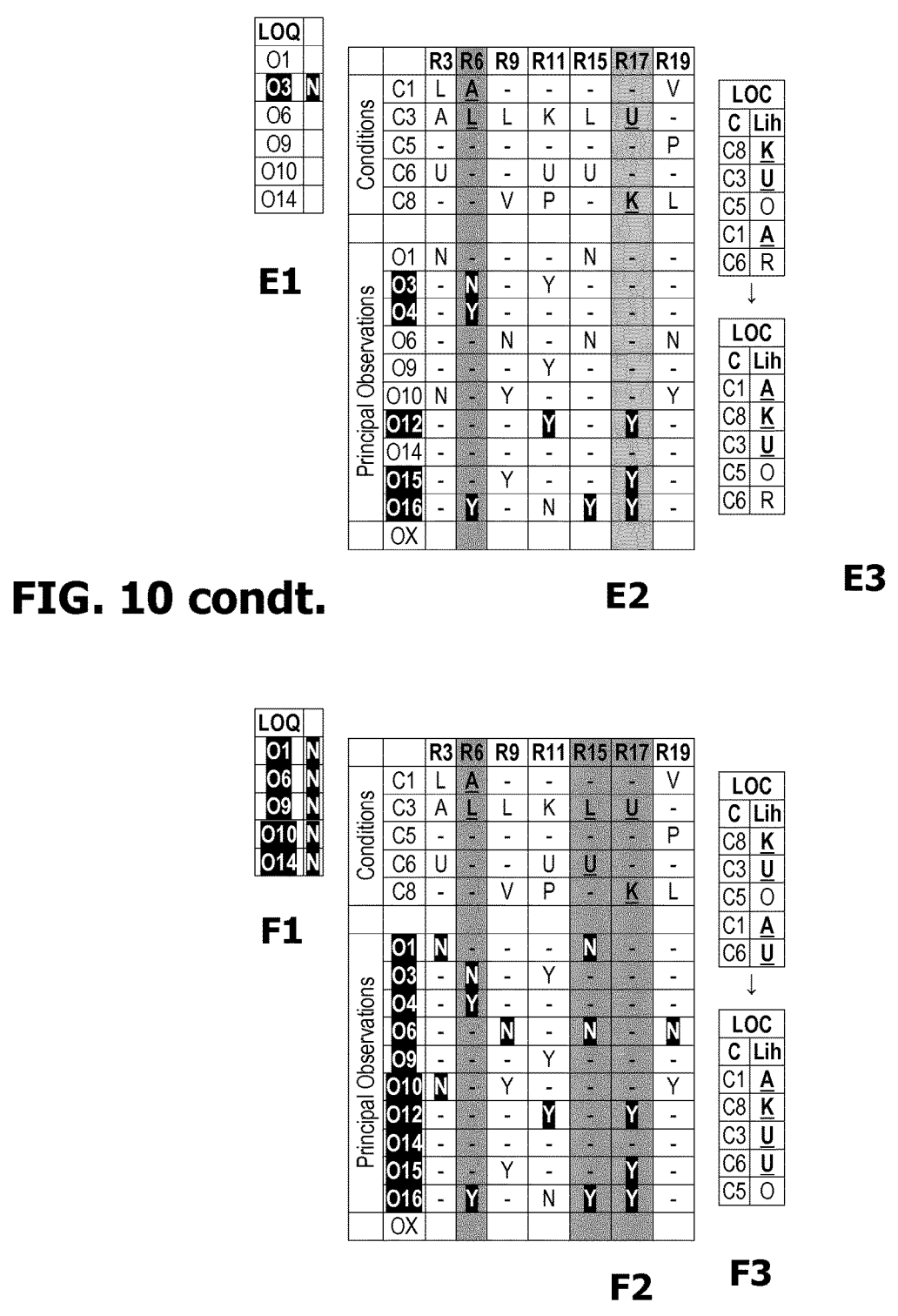

FIG. 10 (A1 to G3) depicts a set of conditions and set of principal observations generated in FIG. 9 A1 to D2, and steps of updating the list of conditions (LOC) and the list of questions (LOQ) according to the selections by the user.

Figure 11:
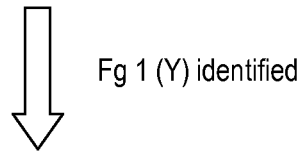

FIG. 11 depicts a possible database structure (A) of principal observations, conditions, associated flag types and statuses, and a set of conditions and set of principal observations (B) selected according to flag Fg1 having status "Y".

Figure 12:
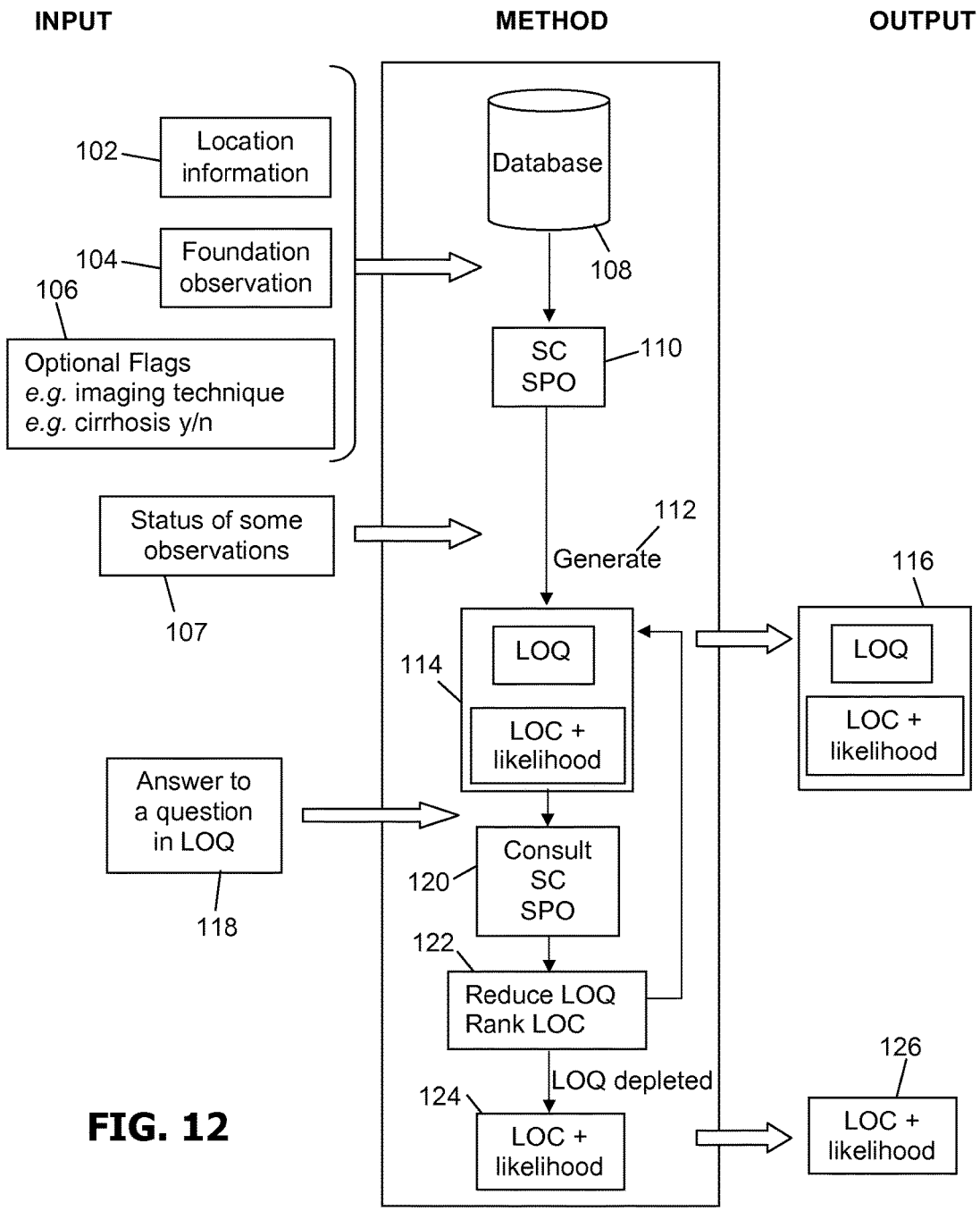

FIG. 12 shows an exemplary work flow of the invention.

Figure 13:
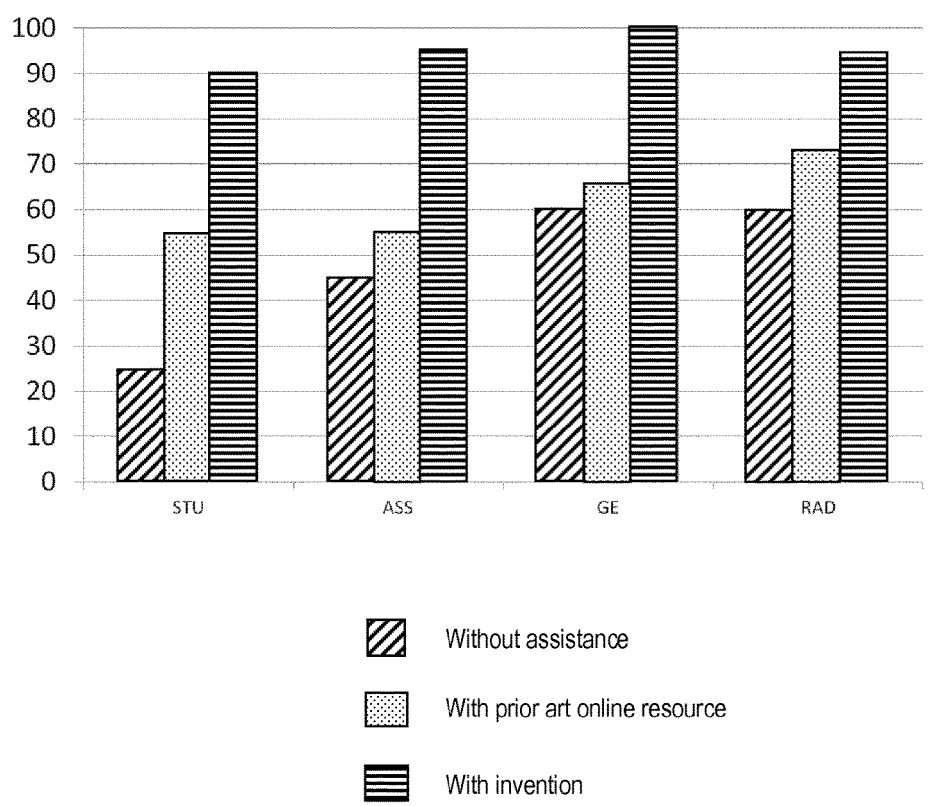

FIG. 13 shows the results of a study of different groups, students (STU), radiology trainees (ASS), gastroenterologists (GE), and radiologists (RAD) and the success rate (%) in correctly identifying a condition in a patent with no assistance, with assistance from the invention, and with assistance from online resources currently preferred by radiologists for diagnostic help.

DETAILED DESCRIPTION OF INVENTION

Before the present method used in the invention is described, it is to be understood that this invention is not limited to particular methods, systems, or devices described, as such methods, systems, and devices may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The present invention relates to a method for assisting a user in determining a medical condition in a subject from one or more medical images. The method is preferably computer implemented. The computer is typically provided with a screen and an input device. The invention is related to the finding by the inventors that a diagnosis of a condition in a patient can be reached with speed and accuracy by presenting the user with a list of questions, LOQ, about the subject that are to be answered with an affirmative indication (Y), a negative indication (N) or an unknown indication (X) by input by the user. Typically the user will respond by manual input such as clicking a mouse, touching a screen, or oral communication. In response to receiving an answer to one question, the method presents the user with a ranked list of conditions, LOC, and also with an updated LOQ wherein at least the answered question has been removed i.e. the LOQ iteratively collapses or reduces in length.

The method accesses a database that contains principal observations, conditions, and sets of rules. Each rule defines a discrete likelihood of a condition (e.g. almost certain (A), likely (L), key diagnostic consideration (K), possible (P), unlikely (U), virtually excluded (V)) as a function of the status of one or more observations (present (Y), not present (N), or not known (X)). There may be 4 to 6 possible likelihoods, preferably 5 (e.g. A, L, K, P, U, V). Each likelihood is different and may be a likelihood in a range from high to low. Multiple rules can be associated with one condition. Multiple conditions can be associated with one rule.

An example of several or a set of rules, SR, is shown with reference to FIG. 1. FIG. 1 shows a possible data structure within the database containing a set of conditions, SC 10 populated by a plurality of conditions (C1 to C5), and a set of principal observations SPO 20 populated by a plurality of principal observations (O1 to O9). Each SC contains a plurality of conditions that are patient-related medical conditions. A condition (e.g. C2), in particular its likelihood (e.g. L), is linked to one or more principal observations (e.g. O9, O6, O4) by an indication of the presence (Y) or absence (N) of the principal observations. Where there is no knowledge (−) of the principal observation, the cell is indicated with a "−"; there is no link present and no data is entered thereto when making the database and SR therein. Within the set of rules, SR, (R1 to R10), each rule links one or more conditions (selected from C1 to C5) to one or more principal observations (selected from O1 to O9). For instance, R1 states that when O1="Y" and O6="N", then C1="L", C2="A", and C4="U".

FIG. 2 shows one condition (C1) in more detail. C1 is associated with 4 separate rules (R1, R2, R5, R8). In R1, the likelihood is "likely (L)" when observation 1 (O1) is present and principal observation 6 (O6) is absent. In R2, the likelihood is "almost certain (A)" when principal observation 2 (O2) is absent and principal observation 3 (O3) is present. According to R5, the likelihood is a "key diagnostic consideration (K)" when principal observation 1 (O1) is present, and principal observation 3 (O3) is present, and principal observation 5 (O5) is absent. R8 defines that the likelihood is "virtually excluded (V)" when principal observation 4 (O4) is absent, and principal observation 6 (O6) is present.

Each principal observation has the possibility to be formulated as a question by the method. The question mainly asks the user whether the principal observation is present (Y), absent (N) or has an unknown status (X). Hence, an inputted status correspond to the presence or absence of the observation, or to an unknown status (not known). Examples and types of principal observations are given below.

Each condition in the SC is assigned one or more rules. Each rule states the circumstances under which a likelihood, for example, one of A, L, K, P, U or V, of the several possible likelihoods, is applicable; the circumstances are the presence (Y) or absence (N) of one or more principal observations in the SPO. Where the status of an observation has an unknown indication, the corresponding rule is not applied. Examples and types of conditions are given below. A rule of the SR is tested against the input of the user; when the user selects all the principal observations from the SPO that happen to be present in a rule of SR, and each and every principal observation has a status also corresponding to the rule, the rule is satisfied and outputs the corresponding conditions and likelihoods. A satisfied rule indicates one or more specified conditions each at a specified likelihood on the one hand, and a specified absence or presence of one or more specified principal observations on the other hand. In FIG. 2, for instance, Rule 1 states that when O1="Y" and O6="N" then C1="L", C2="A" and C4="U". Hence, rule 1 will be satisfied when O1="Y" and O6="N", and will output C1="L", C2="A" and C4="U".

When two or more rules are satisfied and a condition common to both rules has a different likelihood according to each satisfied rule, the method may assign the lowest likelihood to the condition in the LOC. In such case, the method may assign the lowest likelihood to the condition in the LOC in the preference order V, U, P, K, L, A. For instance, in FIG. 1, should rules 5 and 8 be satisfied, C1 may be "K" or "V"; the method may output C1="V" to the LOC. At least some of the observations present in the set of principal observations (SPO) are used to formulate (generate) questions present in the LOQ.

According to one aspect of the invention, the database contains:
  a set of principal observations SPO, each corresponding to a description of a medical-image- or subject-related observation,
  a set of conditions, SC, optionally (see later below) each linked to at least one foundation observation, and
  a set of rules, SR, wherein each rule in the SR links a discrete likelihood of at least one condition with the absence or presence (N, Y) of at least one principal observation.

The SC may be selected or populated from a larger group of conditions in the database. The larger group may be known as a multitude of conditions (MC). The selection may be determined according to the presence of a foundation observation as described later below.

The SPO may be selected or populated from a larger group of principal observations in the database. The larger group may be known as a multitude of principal observations (MPO). The selection may be determined according to the presence of a foundation observation as described later below.

The SR may be selected or populated from a larger group of rules in the database. The larger group may be known as a multitude of rules (MR). The selection may be determined according to the presence of a foundation observation as described later below.

The database is created by one or more expert practitioners. For ease of data entry, the expert may be presented with an editable table, having a configuration similar to that of FIG. 1, or FIG. 7A2. The database allows the creation of principal observations and conditions, and an indication of the relation between them e.g. selection from A, L, K, P, U or V for a condition, and selection from Y, N for the corresponding principal observation. Thereby a multiplicity or set of rules is formed. Where there is no knowledge ("–" or "X") of the principal observation, the cell is indicated with a "–" and no data is entered thereto.

Typically the expert will start from a condition, and associate the status of principal observations to that condition, with an indication of a likelihood per observation.

The database may be provided in any form; typically it is stored on a storage medium such as a magnetic drive or in flash memory and the like. It is within the scope of the invention that the database is present in a working memory of the computer. For instance, when a SC is generated from a MC, or a SPO is generated from a MPO, or a SR is generated from a MR, the SC, SPO and SR may be stored in the working memory of the computer.

Accordingly, the present invention provides a method for assisting a user in determining a medical condition in a subject from one or more a medical images, the method comprising the steps:
i) outputting to the user a list of questions (LOQ) from a database, each question enquiring as to the status of a principal observation in the patient pertinent to the one or more medical images, whereby the status comprises an indication of the presence (Y), absence (N), or lack of knowledge (X) of the principal observation in the patient. Further, the method may further comprise outputting to the user a list of conditions, LOC, from the database, each condition associated with a discrete likelihood. Preferably, the initial number of questions is at least 2.

The method, following step i), may further comprise one or more of the steps:
ii) receiving a response from the user to one of the questions presented in the LOQ, which answer is an indication of the status (Y, N, X) of the principal observation;
iii) updating the list of conditions, LOC, that satisfy the user-indicated status of the principal observation according to the rules linking the SPO and SC, each condition associated with the discrete likelihood;
iv) outputting to the user, at least part, preferably all of the LOC and discrete likelihoods updated;
v) outputting to the user a revised LOQ, wherein at least the question corresponding to the observation status received is removed; and
vi) repeating steps ii) to v), optionally until there are no more questions in the LOQ, thereby arriving at the LOC and discrete likelihoods that satisfy the status of the observations according to the one or more rules.

According to another aspect, the present invention provides a method for assisting a user in determining a medical condition in a subject from one or more a medical images, the method comprising the steps:
i) providing a database containing:
  a set of principal observations, SPO, each corresponding to a description of a medical-image- or subject-related observation,
  a set conditions, SC, and
  a set of rules, SR,
  wherein each rule in the SR links a discrete likelihood of at least one condition in the SC with (only) the absence or presence (e.g. N, Y) of at least one principal observation in the SPO,
ii) generating and outputting a list of conditions, LOC, from the SC and a list of questions, LOQ, from the SO,
iii) receiving an input as to the status (e.g. Y, N, X) of one question in the LOQ,
iv) updating and outputting:
  the LOC (an "updated LOC"), wherein likelihoods for conditions linked to the rules satisfied by status received in step iii) are provided, and
  the LOQ (an "updated LOQ"), wherein at least the question corresponding to the observation status received in step (iii) is removed,
vii) repeating steps v) to vi). Steps v) to vi) may be repeated optionally until there are no more questions in the LOQ. Steps v) to vi) may be repeated until there are no more questions in the LOQ or the user stops.

In any case, user may continue to answer questions until there are no more questions in the LOQ, or may stop answering the questions prior to depletion of question. The method may continue until an indication is received to stop.

The method is preferably performed in the order mentioned above. It will be appreciated that the order of certain steps can be changed within the ordinary activities of the person skilled in the art.

The principal observation is also known as an "observation" herein. Terms relating to the principal observation such as "set of principal observations" (SPO), "subset of principal observations" (SSPO), "linked set of principal observations" (LSPO) and "multitude of principal observations" (MPO) are also known as "set of observations" (SO), "subset of observations" (SSO), "linked set of observations" (LSO) and "multitude of observations" (MO) respectively herein.

The principal observation may be a medical image-related or patient-related observation. The status of principal observation may be identified by the user of the invention by his input, or identified using information from another database, for instance, from a picture archive and communication system (PACS), radiology information system (RIS) or hospital information system (HIS). Typically such databases already contain patient-related information. If the status of the principal observation is supplied from another database, the method may not request its status from the user.

An imaging-related principal observation concerns an identification of one or more abnormalities in a pattern in a medical image, namely in the one or more medical images. The medical image can be obtained by any means of the art. Examples of types of medical images include, but are not limited to computer tomography images (CT or CAT scan), positron emission tomography images (PET scan), magnetic resonance imaging scans (MRI), ultrasound images, X-ray images, histology images. Such images may be combined with computer enhancement methods, computer predictive methods, chemical markers, contrast agents etc., all known to the person skilled in the art. It is an aspect of the invention that the predefined selection of patterns is further defined by the modality of the medical image.

The medical image-related principal observation may be identified, for example, in terms of the type of abnormality. In the case of the liver, an image-related principal observation (abnormality) may be, for example, intralesional fat, bile duct dilatation, "fading" in portal venous and delayed phase, heterogenous hypervascular mass, peripherally enhancing mass, and the like.

The patient-related observations relates to other patient information such as the sex of patient, age, ethnicity, immune status and oncological antecedents. It contains non-image-related information. In the case of the liver, examples of patient-related principal observations include, adolescent or young adult, normal alpha-fetoprotein levels, contraceptive pill intake, use of anabolic steroids, history of melanoma, and the like.

The conditions are medical conditions or dysfunctions in the subject. In the case of the liver, a condition may be, for instance, angiomyolipoma, cholangiocarcinoma (intrahepatic), fibrolamellar hepatocellular carcinoma, focal nodular hyperplasia, hepatocellular adenoma, melanoma metastasis, metastatic cancer, hepatocellular carcinoma, and the like.

The method displays at least part, preferably all of the LOQ to the user. The method may initially display all the questions in the LOQ. The LOQ may be presented to the user as a list wherein a selection indicating presence (e.g. Y), absence (e.g. N), or not known (e.g. X) can be made. Questions in the LOQ of questions may be presented as an elongated list, as a plurality of tiles, or in any other suitable manner. According to one aspect, the input of the status may be selected from a group consisting of presence (e.g. Y), absence (e.g. N), or not known (e.g. X). The input of the status may only be an indication of presence (e.g. Y), absence (e.g. N), or not known (e.g. X). The method may not accept any other status input.

A set of principal observations SPO is used to generate the LOQ. Each question in the LOQ enquires as to the status (e.g. Y, N, X) of a principal observation in regard of the subject. A question in the LOQ is directly based on a corresponding principal observation; in other words a principal observation may be converted to a question. For instance, a principal observation "contraceptive pill intake" may be reformulated as "does the patient take a contraceptive pill" or more simply "contraceptive pill intake?". A question may be posed as text and/or an associated image. For instance, the question "lesion with biliary obstruction" may be accompanied by an image of a lesion with biliary obstruction.

According to one aspect of the invention, all the principal observations in the SPO are reformulated as questions that initially populate LOQ. According to another aspect, some of the principal observations in the SPO are reformulated as questions that initially populate LOQ.

The questions in the LOQ may be presented in any order. The questions in the LOQ may be answered in any order. The selection of the status may be made using an input device such as a mouse, touch screen, computer touch screen, or microphone. In a typical implementation, the LOQ of question is presented as a plurality of tiles, each tile provided with a different question. Selecting a tile (e.g. by rolling a mouse over the tile), reveals the three possible selectable answers (e.g. Y, N, X).

The status of some of the principal observations in the SPO may be determined using information from another database, as mentioned earlier, for instance, from a picture archive and communication system (PACS), radiology information system (RIS) or hospital imaging system (HIS); the remaining observations in the SPO are reformulated as questions that initially populate LOQ, and additionally, the LOC is updated, to contain conditions satisfying the status of the observation according to the rules, each condition associated with the discrete likelihood.

As questions are answered by the user, the LOQ is updated to remove at least the questions that have been answered. The LOQ may further be updated to remove questions belonging to a subset of principal observations (SSPO)—see later below. The LOQ may further be updated to remove one or more questions that would indicate a condition with specific likelihood(s). Preferably, one or more questions are removed that are linked to a condition having received the lowest two likelihood(s), e.g. "U" or "V" above.

The method displays at least part of the LOC, together with the associated likelihood for each condition. The method may display all the conditions in the LOC together with the associated likelihood for each condition. The LOC may be modified to remove conditions with the lowest likelihood(s) as mentioned below. The LOC may be presented to the user as an elongated list. Typically, the list runs in a vertical direction, the most likely condition at the top of the list, and the least likely at the bottom of the lost. The position of the LOC on the computer screen preferably stays essentially constant during the method. After each updating step, the position of the LOC on the computer screen stays essentially constant.

After receiving an input as to the status of a principal observation, the list of conditions, LOC is updated. Specifically, the LOC and associated likelihoods are updated to satisfy the user-indicated status of a selected principal observation according to the rule. In other words, when a rule is satisfied, the likelihood of the conditions specified in the satisfied rule will be updated in the updated LOC.

Besides updating the likelihood of conditions, the updating step may include an ordering or re-ordering of the conditions in order of likelihood. Preferable, the most likely condition is placed first e.g. in the order A, L, K, P, U, V.

Prior to receiving an input as to the status of a principal observation, the conditions in the LOC may be provided with an initial a priori rating. Each condition in the LOC may be assigned an automatically generated a priori rating (APR) based on the selection of the presence of a particular pattern or other observation (foundation observation) in the one or more radiological images in an earlier filtering step discussed later below. The APR may be, for instance, "common" (C), "uncommon" (O), and "rare" (R). In such case, the updated LOCs are iteratively provided with likelihoods that replace the APRs as the status of more observations is established by the present method. Where the LOC contains a mixture of likelihoods and APRs, the conditions in the LOC may ordered as follows: A, L, K, P, C, O, R, U, V, where A, L, K, P, U, V are likelihoods and C, O and R are APRs.

An example of updating the LOC is shown in FIG. 10. FIG. 10 (A2-G2) shows a SC (C1, C3, C5, C6, C8) linked to a SPO (O1-O16) by a SR (R3, R6, R9, R11, R15, R17, R19), a list of questions, LOQ (A1-G1), and a list of conditions, LOC (A3-G3). The each condition in the LOC is assigned an automatically generated a priory rating (APR, "common" (C), "uncommon" (O), and "rare" (R)) as discussed later below. In FIG. 10A1-A3, user selects O16=Y from the LOQ (A1); none of rules R3, R6, R9, R11, R15, R17, or R19 is satisfied (A2); an update of the LOC shows only automatically generated initial a priori ratings (APR) but no likelihoods (A3). In FIG. 10B1-3, O16 is removed from LOQ and the user selects O15=Y (B1); none of rules R3, R6, R9, R11, R15, R17, or R19 is satisfied (B2); an update of the LOC shows no likelihoods (B3). In FIG. 10C1-3, O15 removed from LOQ, user selects O4=Y (C1); none of rules R3, R6, R9, R11, R15, R17, or R19 is satisfied (C2); an update of the LOC shows only automatically generated initial a priori ratings (APR) but no likelihoods. In FIG. 10D1-3, O4 is removed from the LOQ, user selects O12=Y (D1); Rule 17 is satisfied (D2); an update of the LOC shows C8=K and C3=U (D3, upper), ranked most likely first (D3, lower); the likelihoods of C5 and C2 replace the respective APRs. In FIG. 10E1-3, O12 removed from the LOQ, the user selects O3=N (E1); Rule 6 is satisfied (E2); an update of the LOC shows C8=K, C1=A and C3=U (E3, upper), ranked most likely first (E3, lower); the new likelihood of C1 replaces the respective APR. In E2, when both Rules 6 and 17 are satisfied, C3="L" and "U"; the method may select the lowest likelihood so assigning C3=U. In FIG. 10F1-3, O3 is removed from the LOQ, user selects O1=N, O6=N, O9=N, O10=N, O14=N (F1); Rule 15 is satisfied (F2); an update of the LOC shows C8=K, C1=A, C3=U, C6=U (F3, upper) ranked most likely first (F3, upper); the new likelihood of C6=U replaces the respective APR. In F2, when Rules 2, 6 and 7 are satisfied, C3="L", "L" and "U"; the method may select the lowest likelihood so assigning C3=U. In FIG. 10G1-3—the final state—the LOQ is depleted (G1), Rules 6, 15, 17 are satisfied (G2); the LOC shows C8=K, C1=A, C3=U, C6=U, ranked most likely first (G3).

It is appreciated that the method retains an indication of previously-answered questions. Hence, the status of the question received from the user is added the previously received statuses, and the rules applied to the accumulated statuses.

According to one aspect of the invention, two or more principal observations in the SPO constitute a subset of principal observations (SSPO), such that the presence or absence of one principal observation of the SSPO is indicative of the presence or absence of the remaining observations in the SSPO. Accordingly, step v) may result in removal of all questions enquiring as to the status of principal observations in the SSPO, when the answer received in step ii) is an indication of the status of one principal observation of the SSPO.

According to one aspect of the invention, two or more principal observations in the SPO constitute a linked set of principal observations (LSPO), associated to a status (e.g. affirmative indication (Y), a negative indication (N)) of a linking principal observation. An indication of a status (e.g. Y, N) of the linking principal observation will trigger presentation of a linked set of questions LSOQ enquiring as to the status of the LSPO to be answered by the user. As questions within the LSOQ are answered by the user, the LSOQ is modified to remove at least the answered questions. Observations within the LSOQ that are also part of a SSPO may also be removed as the status is provided by the user. The statuses of the LSPO are used to update the LOC that satisfy the user-indicated status of the observation according to the rules. The use of a LSPO and subsequently displayed LSOQ reduces the number of initial questions to be answered by the user.

The number of principal observations and the number of conditions available in the database that are used to populate the respective SPO and SC may be reduced by a pre-filtering, based on a foundation observation.

The foundation observation is typically a predefined pattern in the one or more medical images. A foundation observation may correspond to any fundamental observation concerning an abnormality in the pattern. A foundation observation is selected from the SPO by the expert creating the database based on its diagnostic (discriminative) value. A strong foundation observation significantly reduces the list of related conditions. When an expert observes an abnormality, he will put it in a basic category (e.g. the tendon is thickened) that is equivalent to the foundation observation.

The database may hold a plurality of foundation observations, each associated with one or more conditions and with a principal observation. The database may hold a plurality of foundation observations, each associated with one or more conditions and optionally with a principal observation. Preferably a condition is associated with at least one foundation observation in the database. Hence, the SC may be populated with conditions linked to the indicated foundation observation. Hence, the SPO may be populated with principal observations also linked to the indicated foundation observation. Certain foundation observations may populate a set of foundation observations, SFO, based, for instance, on the location of the one or more medical images (see later below), or more preferably, based on a subset of the SPO.

Hence the method may further comprise the steps:
receiving an indication of the presence of a (e.g. one) foundation observation in the patient,
populating from the database, the SC with conditions associated with the indicated foundation observation.
optionally populating from the database, the SPO with principal observations linked to the indicated foundation observation and at least one condition in the SC Identification of the foundation observation may be performed prior to step i) above.

According to one aspect, a set of foundation observations (SFO) containing one or more (preferably at least two) foundation observations, optionally based on location, is preferably presented to the user. Where the foundation observation is indicated by the user as being present in the patient, the conditions associated with the identified foundation observation are used to populate the SC. The user preferable identifies the presence of one foundation observation, however, it is within the scope that several (e.g. 2, 3, 4, or more) foundation observations are identified by the user.

It is an aspect of the invention that foundation observation in the SFO is automatically identified from a medical image, for instance using pattern recognition or using a camera worn by the user (e.g. Google Glass). Automatic pattern recognition technology is well known in the art, for instance, from U.S. Pat. No. 8,081,811 B2.

Preferably the condition(s) associated with the identified foundation observation are used to populate the SC. Subsequently, the principal observations linked by rules to the conditions in the SC so-populated are used to populate the SPO. It is a further aspect of the invention that some principal observations in the database are associated with some foundation observations. Hence, the observations used to populated the SPO may be refined to include only those associated with the identified foundation observation. Hence the method may further comprise the step of reducing the SPO to include only observations associated with the identified foundation observation(s).

The method may present the user with a set of foundation observations, SFO, to which the user selects one pertinent to the patient.

Alternatively, to assist the user, one or more of the foundation observations in the SFO may belong to a hierarchical decision tree in the database, having upper branches (top of the tree) and lower branches (base of the tree) and end branches at which the decision is made. A foundation observation is represented by branch ends. One or more upper branches contain basic observations pertinent to the patient. Basic observations in the upper branches are more generalized observations concerning the pattern, increasing in specificity towards the lower branches. The user may indicates the presence of the basic observations starting from the top of the tree, leading to indications of the presence of more specific basic observation, and eventually to a choice of a foundation observation.

Figure 3:
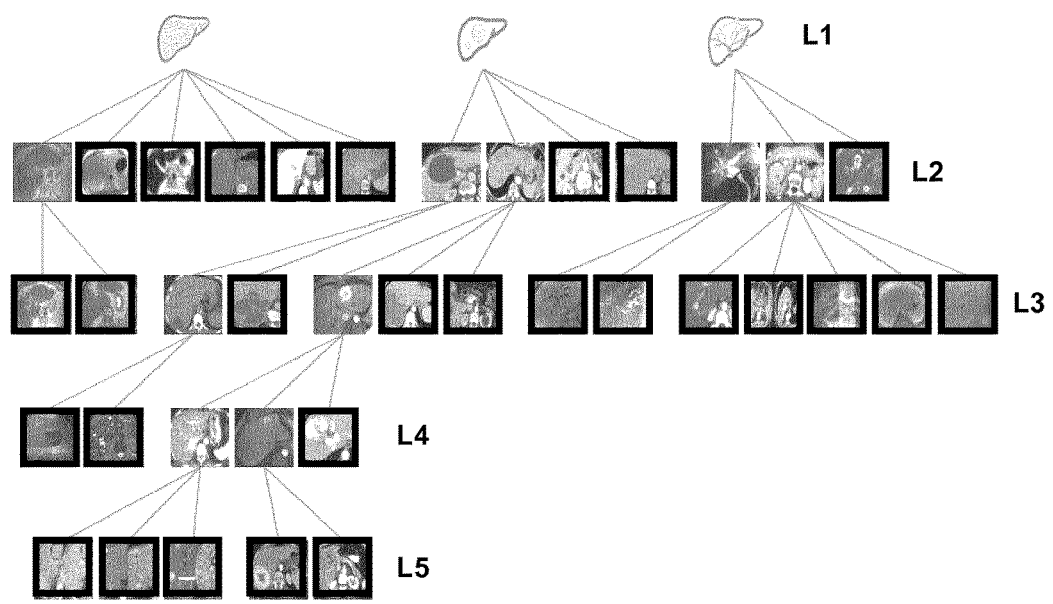
FIG. 3 depicts an exemplary set of foundation observations (thick black framed boxes), some of which belong to a hierarchy of choices.

FIG. 3 shows a hierarchical organization whereby the foundation observations at the branch ends are indicated with black edged boxes. Five levels (L1 to L5) are hierarchy indicated. L1 might be, for instance an observation concerning the presence of a diffuse pattern, a focal/multifocal pattern or a vascular/bilary pattern, and L2 to L4 progressively determine the more specific features of the radiological pattern.

Figure 4:
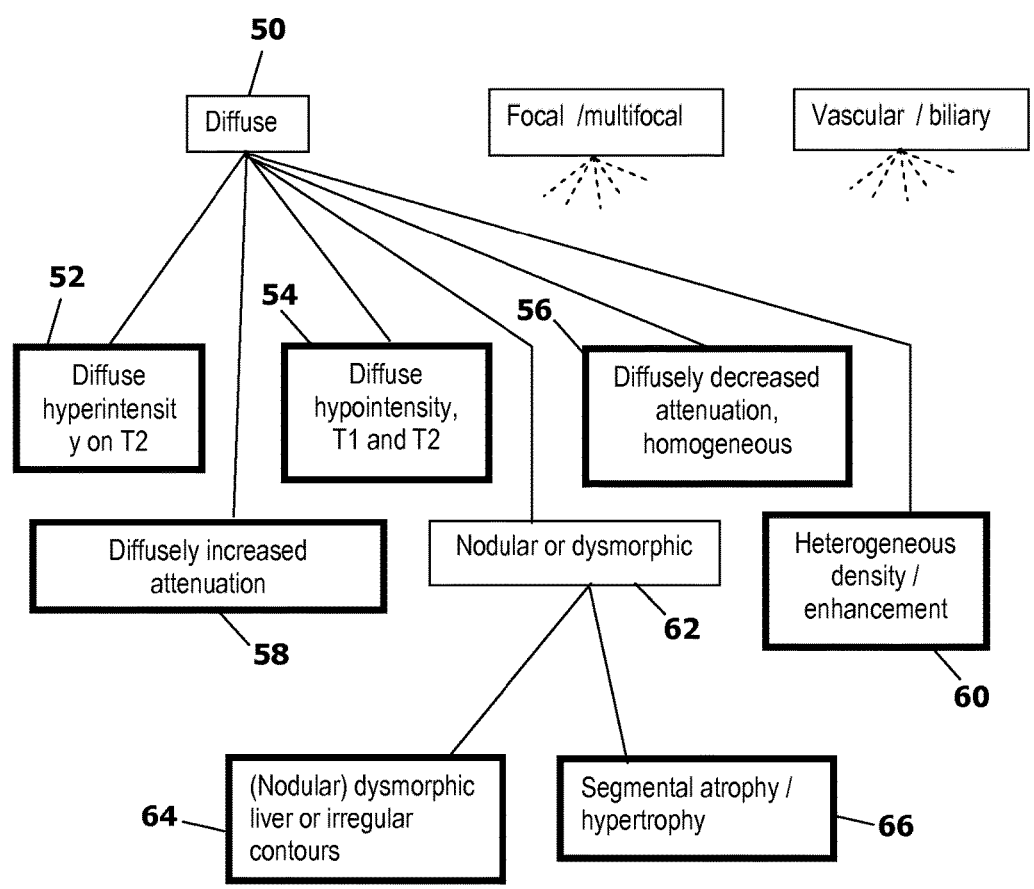
FIG. 4 depicts an exemplary set of foundation observations in text (thick black framed boxes), some of which belong to a hierarchy of choices.

FIG. 4 shows an example of a hierarchical tree, starting with the presence of a generalized observation that is a diffuse pattern 50. The user can select a foundation observation from any of the thick-lined boxes 52, 54, 56, 58, 60, 64, 66. Boxes 64 and 66 are hierarchical relation to box 62.

Examples of foundation observations applicable to the liver, include Diffuse hyperintensity on T2, Diffuse hypointensity, T1 and T2, Diffusely decreased attenuation, Diffusely increased attenuation, Heterogeneous density/enhancement, (Nodular) dysmorphic liver or irregular contours, Segmental atrophy/hypertrophy.

Hence the method of the invention may further comprise the steps of,
a) requesting from the user, an indication of the presence of a (e.g. one) foundation observation in the patient,
b) populating from the database, the SC with conditions associated with the indicated foundation observation.

Step a) may further comprise the step of displaying all foundation observations in the SFO, and requesting the user to select a (e.g. one) foundation observation present in the patient. Alternatively, step a) may further comprise the step of presenting the user with a series of choices, arranged hierarchically in increasing specificity, that guide the user towards a selection of a (e.g. one) foundation observation from the SFO present in the patient. The choices are preferably present stepwise i.e. a further choice is presence once a previous choice has been made.

It is an aspect of the invention that each condition linked to a foundation observation is given an a priori rating. This a priori rating is different from the likelihood as described herein. For instance, it does not take into account inputted principal observations and relationship with the rules. An a priori rating is a more general likelihood. An a priori rating may be present for each condition in the group of conditions sharing the same foundation observation. For instance, "hepatocellular carcinoma" (condition) may have a "common" a priori rating when a "hyperenhancing mass" (foundation observation) is seen. Hence, these a priori ratings are specific for a combination of foundation observation/condition. A condition can have a different a priori rating when a different foundation observation is present. There may be 1, 2, 3, 4, 5, 6, 7 or more categories of an a priori ratings, preferably between 3 and 5, most preferably 3. The categories may be, from most common to least common, "common", "uncommon", and "rare". Once the status of one or more principal observations have been provided, an a priori rating for a condition may be replaced by the likelihood determined by the rules.

A single condition may be linked to only one foundation observation by one APR. A single condition may be linked to two or more (e.g. 3, 4, 5, 6) different foundation observations, wherein there is only one APR for each foundation observation linked to the single condition. A single foundation observation may be linked to two or more (e.g. 3, 4, 5, 6) different conditions, wherein there is only one APR for each condition linked to the single foundation observation. More than one condition in the SC may be so linked, optionally each and every condition in the SC may be so linked, preferably a majority of conditions in the SC may be so linked. A plurality of conditions in the MC may be linked to a plurality of foundation observations in the SFO by discrete a priori ratings, APRs, wherein each foundation observation is linked to the corresponding condition by one APR.

Figure 5:
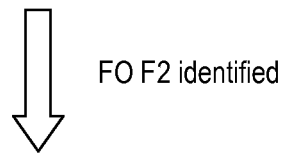
FIG. 5 depicts a possible database structure (A) of principal observations, conditions, associated likelihoods and observation statuses, together with foundation observations (FO) and a priori ratings (APR), and a set of conditions and set of principal observations (B) selected according to foundation observation F2, giving rise to different a priori ratings.

FIG. 5 shows an exemplary part of a database (FIG. 5A) containing conditions (C6 to C10) associated with principal observations (O11 to O19) by rules (Y, N) and likelihoods (A, L, K, P, U, V). An additional field for each condition is provided (FO/APR) for entry of a foundation observation (FO) paired with an a priori rating (APR). Foundation observation "F1" may be, for instance "hyper-enhancing mass", foundation observation "F2" might be, for instance "cystic", foundation observation "F3" might be, for instance "hypo-enhancing". F2 is paired with a priori rating "O" (uncommon) when the condition is C7. F2 is paired with a different a priori rating ("C"—common) when the condition is C9, and a different a priori rating "R" (rare) when the condition is C10. When the foundation observation (FO) is identified as F2, for instance, by the user or from other patient-related information, the conditions used to populated the SC (10) is reduced (FIG. 5B) and there is a concomitant reduction in the number of principal observations in the SPO 20. The user may be presented with an a priori rating from the APR column of the SC 10.

The number of principal observations and the number of conditions available in the database that are used to form the respective SPO and SC may be reduced by a pre-filtering, based on an indication of the location one or more medical images, which location is a bodily location. There may be a pre-defined set of bodily locations. The principal observations and/or conditions may be associated with a location in the database. Where the location is indicated, the principal observations and conditions associated with the indicated location are used to populate the SPO and SC that are used to formulate the LOQ. The location may be used to populate the SFO, which in turn is used to populate the SC, which in turn determines the SPO. More preferably, the SFO is a subset of the SPO (described later below).

The indication of the location can be provided by the user, or can be provided using information from another database, for instance, from a picture archive and communication system (PACS), radiology information system (RIS) or hospital imaging system (HIS).

Examples of locations include liver, knee, prostate, rectum, breast, lung, ovary, kidney, brain, and the like.

Hence the method of the invention may further comprise the steps:

receiving an indication of location of the one or more medical images in the patient from a pre-defined list containing one or more locations, and populating from the database, the SC with conditions associated with the indicated location.

Alternatively, the method may further comprise the steps:

receiving an indication of the location of the one or more medical images in the patient from a pre-defined list containing one or more locations, and populating the SFO with foundation observations associated with the indicated location.

Preferably, the SC is populated based on an indication of both a foundation observation and a location. According to one aspect, the method of the invention further comprises the steps:

receiving an indication of location of the one or more medical images in the patient from a pre-defined list containing one or more locations, populating from the database, the SFO with foundation observations associated with the indicated location receiving an indication of the presence of a (e.g. one) foundation observation in the patient from the SFO, populating from the database, the SC with conditions associated with the indicated foundation observation.

Figure 6:
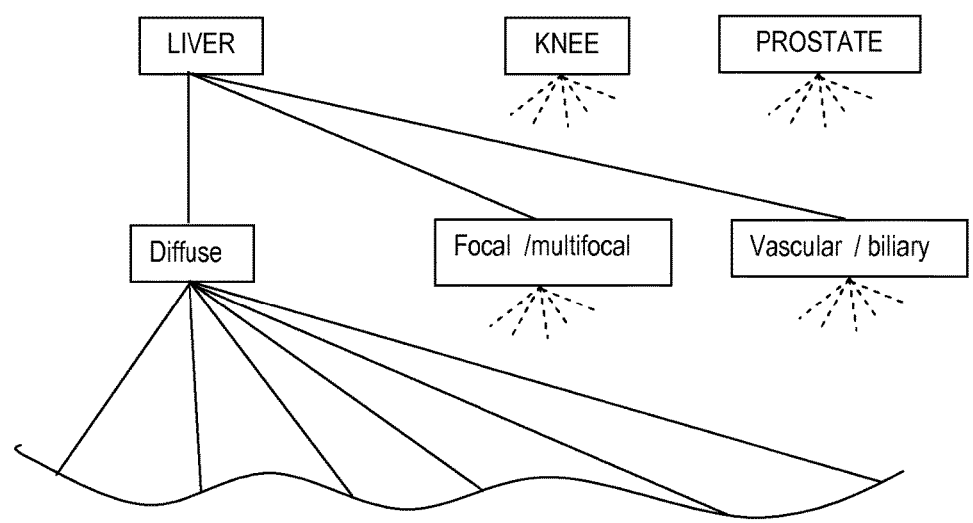
FIG. 6 depicts an exemplary group of locations and associated set of foundation observations for one location (liver).

Identification of the location is preferably performed prior to selection of the foundation observation above. FIG. 6 shows exemplary locations (liver, knee, prostate) and a set of foundation observations (diffuse, focal/multifocal, vascular/biliary) associated with the liver location.

Advantageously, a foundation observation in the SFO may correspond to a principal observation. Each foundation observation may correspond to a principal observation, and there is a smaller number of foundation observations in the SFO than principal observations in the database. It is preferred that foundation observations correspond only to principal observations that are a medical-image-related observations. It is preferred that foundation observations correspond only to principal observations that are predefined patterns in the one or more radiological images.

The SFO may be used to generate a list of foundation observations, LFO. The LFO may be presented (outputted) to the user for selection of whether the foundation observation (principal observation) is present. The LFO may take the form of the hierarchical tree described above, for instance, in FIGS. 3 and 4.

Selection of a foundation observation is equivalent to an indication of a present (Y) status of the principal observation. According to the present method, rules which are not linked to the foundation observation (principal observation), more in particular to the present (Y) status are excluded from further steps in the method. By excluding unlinked rules, the number of conditions in the SC and the number of principal observations in the SPO can be greatly reduced.

According to one aspect of the invention, the database contains a multitude of principal observations, MPO, each corresponding to a description of a medical-image- or subject-related observation. The database may further comprise a multitude of foundation observations, MFO, some of which form the SFO and correspond to a predefined subset of the MPO, and used to generate the LFO. As mentioned earlier, it is preferred that foundation observations in the SFO correspond only to principal observations that are medical-image-related observations. Hence, preferably the SFO is a predefined subset of principal observations in the MPO, insofar as observations in the SFO correspond to principal observations in the MPO that only are medical-image-related observations (and that are not patient-related observations). It also is within the scope of the invention that the predefined subset of principal observations in the MPO correspond to principal observations in the MPO that are medical-image-related and/or patient-related observations. The database may further comprise a multitude of conditions, MC, each linked to at least one foundation observation. The database may further comprise a multitude of rules, MR, wherein each rule in the MR links a discrete likelihood of at least one condition with the absence or presence (N, Y) of at least one principal observation.

A satisfied rule indicates one or more specified conditions each at a specified likelihood on the one hand, and a specified absence or presence of one or more specified principal observations on the other hand.

The method receives an input of a selection of at least one FO from the LFO that is pertinent to the one or more medical images of the subject. After receiving an input of a selection of at least one FO from the LFO, the method may proceed with generating the SC from the MC; typically the SC contains less conditions than in the MC. Further, the SR may be generated from the MR; typically the SR contains less rules than in the MR. Further, the SPO may be generated from the MPO; typically the SPO contains less principal observations than in the MPO.

In generating the SC, conditions not linked to the selected FO are excluded. Further, conditions that are no longer linked to rules in the SR are excluded.

In generating the SR, rules that are not linked to the presence of the selected FO are excluded. In generating the SR, preferably, at least rules that are not linked to the presence of the selected FO are excluded. Selection of a foundation observation is equivalent to an indication of a present (Y) status of the corresponding principal observation. More in particular, at least rules that are not linked to the presence (Y) of the PO associated with the FO are excluded.

In generating the SPO, observations not linked to the rules in the SR are excluded.

As explained elsewhere, it is an aspect of the invention that each condition linked to a foundation observation is given an a priori rating. This a priori rating is different from the likelihood as described herein. For instance, it does not take into account inputted principal observations and relationship with the rules. An a priori rating is a more general likelihood. An a priori rating may be present for each condition in the multitude or set of conditions sharing the same foundation observation. A condition can have a different a priori rating when a different foundation observation is present. There may be 1, 2, 3, 4, 5, 6, 7 or more categories of an a priori ratings, preferably between 3 and 5, most preferably 3. The categories may be, from most common to least common, "common" (C), "uncommon" (O), and "rare" (R). Once the status of one or more principal observations have been provided, an a priori rating for a condition may be replaced by the likelihood determined by the rules.

A single condition in the MC may be linked to one foundation observation in the SFO by only one APR. A single condition in the MC may be linked to two or more (e.g. 3, 4, 5, 6) different foundation observations in the SFO, wherein there is only one APR for each foundation observation linked to the single condition. A single foundation observation in the SFO may be linked to two or more (e.g. 3, 4, 5, 6) different conditions in the MC, wherein there is only one APR for each condition linked to the single foundation observation. More than one condition in the SC in the MC may be so linked, optionally each and every condition in the SC may be so linked, preferably a majority of conditions in the SC may be so linked.

A single condition in the SC may be linked to one foundation observation by only one APR. A single condition in the SC may be linked to two or more (e.g. 3, 4, 5, 6) different foundation observations in the SFO, wherein there is only one APR for each foundation observation linked to the single condition. A single foundation observation in the SFO may be linked to two or more (e.g. 3, 4, 5, 6) different conditions in the SFO, wherein there is only one APR for each condition linked to the single foundation observation. More than one condition in the SC may be so linked, optionally each and every condition in the SC may be so linked, preferably a majority of conditions in the SC may be so linked.

Hence, one aspect relates to a method for assisting a user in determining a medical condition in a subject from one or more medical images, the method comprising the steps:
i) outputting from a database a list of foundation observations, LFO, corresponding to a set of foundation observations, SFO, which SFO is a predefined subset of a multitude of observations, MO, each observation in the MO corresponding to a description of a medical-image- or subject-related observation,
ii) receiving an input of a selection of at least one foundation observation from the LFO,
iii) generating:
   a set of conditions SC linked to the selected FO in a database,
   a set of rules, SR linked to the selected FO in the database, and
   from the MO, a set of observations, SO linked the SR in the database.

The SC, SR and SO are used in subsequent steps in which the LOQ and LOC are generated, updated and presented to the user. These steps are described elsewhere herein. For instance, the further steps may comprise:
iv) generating and outputting a list of conditions LOC from the SC and a list of questions LOQ from the SO,
v) receiving an input as to the status of one question in the LOQ, whereby the status is an indication of the presence, absence or unknown status in regard of the subject,
vi) updating and outputting:
   the LOC, wherein likelihood(s) for condition(s) linked to the rules satisfied by status received in step (v) are provided, and
   the LOQ, wherein at least the question corresponding to the observation status received in step (v) is removed,
vii) repeating steps v) to vi) optionally until there are no more questions in the LOQ.

A further aspect relates to a method for assisting a user in determining a medical condition in a subject from one or more medical images, the method comprising the steps:
i) outputting to the user a list of foundation observations, LFO, from a database, wherein the database contains:
   a multitude of observations, MO, each corresponding to a description of a medical-image- or subject-related observation,
   a set of foundation observations, SFO, corresponding to a predefined subset of the MO, and used to generate the LFO,
   a multitude of conditions, MC, each linked to at least one foundation observation,
   a multitude of rules, MR,
      wherein each rule in the MR links a discrete likelihood (e.g. A, L, K, P, U, V) of at least one condition with (only) the absence or presence (e.g. N, Y) of at least one observation,
ii) receiving an input of a selection of at least one FO from the LFO,
iii) generating:
   a set of conditions, SC from the MC, wherein conditions not linked to the selected FO are excluded,
   a set of rules, SR from the MR, wherein rules that are not linked to the observation corresponding to the presence of the selected FO are excluded,
   a set of observations, SO from the MO, wherein observations not linked to rules present in the SR are excluded, The SC, SR and SO are used in subsequent steps in which the LOQ and LOC are generated, updated and presented to the user. These steps are described elsewhere herein. For instance, the further steps may comprise:
iv) generating and outputting a list of conditions LOC from the SC, and a list of questions, LOQ from the SO,
v) receiving an input as to the status (e.g. Y, N, X) of one question in the LOQ whereby the status is an indication of the presence, absence or unknown status in regard of the subject,
vi) updating and outputting:
   the LOC (an "updated LOC"), wherein likelihood(s) for condition(s) linked to the rules satisfied by status received in step (v) are provided, and
   the LOQ (an "updated LOQ"), wherein at least the question corresponding to the observation status received in step (v) is removed,
vii) repeating steps v) to vi) optionally until there are no more questions in the LOQ.

A plurality of conditions in the SC may be linked to a plurality of foundation observations in the SFO by discrete a priori ratings, APRs, wherein each foundation observation is linked to the corresponding condition by one APR. The number of categories of discrete a priori ratings is between 3 and 5, preferably 3. Each condition in the LOC in step iv)

is initially assigned the corresponding a priori rating according to the at least one FO selected from the LFO in step ii) and the links between the plurality of conditions in the SC and plurality of foundation observations in the SFO of described above. The likelihood(s) for condition(s) provided in step vi) replace the a priori rating initially assigned to the same condition. A satisfied rule indicates one or more specified conditions each at a specified likelihood on the one hand, and a specified absence or presence of one or more specified principal observations on the other hand, FIG. 7A2 is an exemplary depiction of a MC (conditions, C1 to CX . . . ), MPO (principal observations, O1 to OX) and a MR (R1 to RX . . . ), wherein each rule in the MR links a discrete likelihood (A, L, K, P, U, V) of at least one condition with the absence or presence (N, Y) of at least one principal observation. A condition in the MC links one, preferably only one discrete a priori rating (APR) (e.g. common "C", uncommon "O", or rare "R") to a foundation observation (column FO/APR). Only 2 foundation observations (F1, F2) are shown for economy of space; FIG. 8A2 shows an expanded FO/APR segment containing additional foundation observations (F1 to F7 and FX . . . ). In FIG. 7A2 some principal observations in the MPO are linked to a foundation observation (column FO). FIG. 7A1 depicts a LFO, presented to the user for selection of a foundation observation.

The user selects a FO from the LFO (FIG. 7131, C1) that is "F2", and conditions not linked to the selected FO (column F2, not linked conditions "–") are excluded from the SC so formed; the excluded conditions (C2, C4, C7, C9) are indicated with diagonal shading, and the included conditions that form the SC (C1, C3, C5, C6, C8) have no diagonal shading. The result of the exclusion is shown in FIG. 7C2 having a reduced number of conditions, and having generated a SC. Further, APRs for each of the conditions is shown in column FO/APR. As a consequence of removing C2, C4, C7, C9, R13 is not linked to any rule (FIG. 7C2, diagonal shading); hence R13 may be excluded (FIG. 7D2) from the SR.

FIGS. 8 A1, B1 depict the same LFOs as in FIG. 7B1, C1 and the selection of "F2", and FIG. 8 B2 further shows an expanded view of the MFO (column FO/APR). In selecting F2, conditions not linked to F2 are excluded (FIG. 8 B2, diagonal shading) as already shown in FIG. 7B2. The LOC is populated with the remaining conditions (FIG. 8 B2a, B2b), and the conditions in the LOC are ordered from, highest rating condition to lowest (i.e. in order C, O, R) (FIG. 8 B3).

FIG. 9 shows an exemplary sequence of steps that leads to a reduction in the number of rules i.e. to the generation of the SR. The user selection of F2 in FIG. 9A1, corresponds to O15 in the MPO shaded as a grey row (FIG. 9A2). Rules in the MR that are not linked to the presence (Y) of the selected FO are excluded; cells in row O15 marked with a "–" are not linked to a rule. Hence, R1, R2, R4, R7, R8, R10, R12, R14, R16, R18 and R20 are excluded (diagonal shading). The result of the exclusion is shown in FIG. 9B2, wherein the rules form the SR. As a result of the exclusion of R1, R2, R4, R7, R8, R10, R12, R14, R16, R18 and R20, principal observations O2, O5, O8, O11 and O13 (diagonal shading) no longer have rules attached to them, hence these are further excluded from the SPO, the result of which is shown in FIG. 9C2. FIG. 9C2 shows a final result of selection using a foundation observation, namely, a SR, wherein each rule in the SR links a discrete likelihood (A, L, K, P, U, V) of at least one condition in the SC with the absence or presence (N, Y) of at least one principal observation in the SPO, and each condition in the SC is linked to an APR.

The number of principal observations and the number of conditions available in the database that are used to form the respective SPO and SC may be further reduced by a pre-filtering, based on the status of a flag. A flag is an indicator, and is generally of absent, present, or unknown status. The principal observations and/or conditions may be associated with a flag in the database.

Where the flag status is indicated, the principal observations and conditions associated with the indicated flag status are used to populate the SPO and SC that are used in step i) to formulate the LOQ. Examples of flags include imaging technique, and presence of a specific condition of the patient such as cirrhosis. The status of a flag may be selected from a pre-defined list.

The indication of a flag status may be received from the user, for instance, by manual input. Alternatively, the indication of a flag status may be received from information present in another database, for instance, from a picture archive and communication system (PACS), radiology information system (RIS) or hospital imaging system (HIS).

According to one aspect, the flag is indication of the imaging technique used to acquire a medical image that forms the basis of a foundation observation and an image-related principal observation. Examples of imaging techniques as mentioned above include to computer tomography images (CT or CAT scan), positron emission tomography images (PET scan), magnetic resonance imaging scans (MR), ultrasound images (US), X-ray images. Such images may be combined with computer enhancement methods, computer predictive methods, chemical markers, contrast agents etc., all known to the person skilled in the art. Preferably, a flag that is an indication of CT, US or MR is associated with the foundation observation and/or image-related principal observation.

Hence the method of the invention may further comprise the steps of,
  receiving, an indication of imaging technique(s) used to obtain the one or more medical images,
  populating from the database, the SPO and SC with principal observations and/or conditions associated with the selected imaging technique(s).

Receiving an indication of the imaging technique is preferably performed prior to selection of the foundation observation. Preferably, the SPO and SC is populated based on an indication of a location, a foundation observation, and an imaging technique.

According to another aspect, the flag is indication of the status (e.g. presence or absence) of a specific condition in a patient (e.g. cirrhosis).

Hence the method of the invention may further comprise the steps:
  receiving an indication of the status (e.g. presence or absence) of a specific condition in the patient,
  populating from the database, the SPO and/or SC with principal observations and/or conditions associated with the status (e.g. presence or absence) of this condition.

An indication of the flag status is preferably received prior to selection of the foundation observation. Preferably, the SPO and SC are populated based on an indication of a location, a foundation observation, an imaging technique, and optionally another flag status.

FIG. 11 shows an exemplary part of a database (FIG. 11A) containing conditions (C20 to C23) associated with principal observations (O21 to O29) by rules (Y, N) and likelihoods (A, L, K, P, U, V). An additional field for each principal observation is provided (Flag (status)) for entry by the expert of a flag type (e.g. Fg1, Fg2, Fg3, Fg4) and a corresponding status (e.g. Y, N, black white). Fg1 might be, for instance cirrhosis. When the flag identified along with its status (e.g. FG1 is Y) is identified, for instance, by the user or from other patient-related information, the number of principal observations used to populate the SPO (20) is reduced (FIG. 11B).

An exemplary workflow of the method of the invention is provided in FIG. 12. Location information 102, selection of a foundation observation 104, and the status of one of more flags (e.g. imaging technique, absence or presence of cirrhosis in the case the location is the liver) 106 are provided as input (e.g. by the user as input or from another database). The method populates a set of principal observations SPO and related a set of conditions SC 110 by accessing a database 108. The SC are linked to the SPO by virtue of the rules (e.g. as shown in FIG. 1). Optionally, the status of some of the principal observations may be already be known from another database—this information may be provided 107 to the method. The SPO and SC are used to generate 112 a list of questions LOQ and list of conditions together with their likelihoods 114, which is outputted to the user 116. Where the status of a principal observation is known already from 107, the information is used to modify the LOQ and LOC 122 outputted to the user 116. The user answers one of the questions in the LOQ to indicate the status of the principal observations. The method consults 120 the SPO and SC, and updates the LOQ and LOC 122 according on the rules (e.g. as shown in FIG. 1), namely by reducing the LOQ and re-ranking, if necessary, the LOC. The user can stop at any time. The method ends when there are no more questions, with a ranked list of condition 124 which is outputted to the user 126.

In practice, each question in the LOQ may be presented in a user interface as a tile; rolling the mouse over the tile reveals the status to choose from (Y, N, X), clicking the status causes updating of the LOC and the LOQ.

The present invention also provides a computer program, or a computer program product directly loadable into the internal memory of a computer, or a computer program product stored on a computer readable medium, or a combination of such computer programs or computer program products, configured for performing the method as described herein.

The present invention also provides a device configured for performing the method as described herein. The device typically comprises a computer processor and data storage operatively linked to the computer processor. The device further comprises a computer screen and an input means such as a mouse, keyboard, touch screen and the like.

This present method provides a user-friendly easy-to-use system that can be used in complex situations. For instance, there may be 150 different conditions in the liver, at least 100 possible types of observations (abnormalities); one abnormality may correspond to up to 30 possible diseases; in order to determine the likelihood of these diseases, there may be 50 or more relevant questions. No methodology has been described in prior art to make a diagnostic support system that can deal with this complexity while providing a high level of user friendliness.

The inputting of data, by selection from a choice of three possible status indications (Y, N, X) of the question/observation, together with a "collapsing LOQ" greatly simplifies the data entry process for the user. He is confronted with less questions after each input. By simultaneously providing feedback as to the condition considered most likely and unlikely in the LOC after an input, the user is constantly kept informed of the medical conditions ranking at any time. Additionally, he can determine for himself which further questions from the LOQ to answer, and whether to exit the method early or not. The user is guided towards a diagnosis based on previous answered questions, but he can choose in which order to answer the questions, allowing flexibility according to the information and knowledge he has at hand.

In trials, when difficult cases are presented, the system obtains an average accuracy of 90% with radiologists and non-radiologists (compared with an accuracy of 60% using an unassisted user).

FIG. 13 shows the results of trials of the invention with different groups of users having different degrees of experience, namely medical students (least experienced), radiology trainees, gastroenterologists and radiologists (most experienced). A comparison with currently available resources for online diagnostic support is shown, and a comparison with no assistance is also shown. In FIG. 13, the invention obtains a correct diagnosis at least 90% of the time in all user groups.

The invention claimed is:

1. A method for assisting a user in determining a medical condition in a subject from one or more medical images, the method comprising the steps:
   i) outputting to the user a list of foundation observations, LFO, from a database, wherein the database contains:
      a multitude of observations, MO, each corresponding to a description of a medical-image- or subject-related observation,
      a set of foundation observations, SFO, corresponding to a predefined subset of the MO, and used to generate the LFO,
      a multitude of conditions, MC, each linked to at least one foundation observation,
      a multitude of rules, MR,
         wherein each rule in the MR links a discrete likelihood of at least one condition with the absence or presence of at least one observation,
   ii) receiving an input of a selection of at least one FO from the LFO,
   iii) generating:
      a set of conditions, SC, from the MC, wherein conditions not linked to the selected FO are excluded,
      a set of rules, SR, from the MR, wherein rules that are not linked to the presence of the selected FO are excluded, and
      a set of observations, SO, from the MO, wherein observations not linked to rules present in the SR are excluded,
         wherein a plurality of conditions in the SC is linked to a plurality of foundation observations in the SO by discrete a priori ratings, APRs, wherein each foundation observation is linked to the corresponding condition by one APR,
   iv) generating and outputting a list of conditions LOC from the SC, and a list of questions, LOQ from the SO, wherein each condition in the LOC is initially assigned the corresponding APR,
   v) receiving an input as to the status of one question in the LOQ whereby the status is an indication of the presence, absence or unknown status in regard of the subject, vi) updating and outputting:
   the LOC, wherein likelihood(s) for condition(s) linked to the rules satisfied by status received in step (v) are provided, the likelihood(s) replacing the APR initially assigned to the same condition in step (iv) and wherein a satisfied rule indicates one or more specified conditions each at a specified likelihood on the one hand, and a specified absence or presence of one or more specified observations on the other hand, and
   the LOQ, wherein at least the question corresponding to the observation status received in step (v) is removed,
vii) repeating steps v) to vi) such that the LOQ iteratively reduces in length optionally until there are no more questions in the LOQ.

2. The method according to claim 1, wherein the number of categories of discrete a priori ratings is between 3 and 5.

3. The method according to claim 1, wherein the number of discrete likelihoods is between 4 and 8.

4. A method for assisting a user in determining a medical condition in a subject from one or more medical images, the method comprising the steps:
   i) outputting to the user a list of foundation observations, LFO, from a database, wherein the database contains:
      a multitude of observations, MO, each corresponding to a description of a medical-image- or subject-related observation,
      a set of foundation observations, SFO, corresponding to a predefined subset of the MO, and used to generate the LFO,
      a multitude of conditions, MC, each linked to at least one foundation observation,
      a multitude of rules, MR,
         wherein each rule in the MR links a discrete likelihood of at least one condition with the absence or presence of at least one observation,
   ii) receiving an input of a selection of at least one FO from the LFO,
   iii) generating:
      a set of conditions, SC, from the MC, wherein conditions not linked to the selected FO are excluded,
      a set of rules, SR, from the MR, wherein rules that are not linked to the presence of the selected FO are excluded, and
      a set of observations, SO, from the MO, wherein observations not linked to rules present in the SR are excluded,
      wherein a plurality of conditions in the SC is linked to a plurality of foundation observations in the SO by discrete a priori ratings, APRs, wherein each foundation observation is linked to the corresponding condition by one APR,
   iv) generating and outputting a list of conditions LOC from the SC, and a list of questions, LOQ from the SO,
   v) receiving an input as to the status of one question in the LOQ whereby the status is an indication of the presence, absence or unknown status in regard of the subject,
   vi) updating and outputting:
      the LOC, wherein likelihood(s) for condition(s) linked to the rules satisfied by status received in step (v) are provided, the likelihood(s) replacing the APR initially assigned to the same condition in step (iv), and
      the LOQ, wherein at least the question corresponding to the observation status received in step (v) is removed,
   vii) repeating steps v) to vi) such that the LOQ iteratively reduces in length optionally until there are no more questions in the LOQ,
   wherein each condition in the LOC is initially assigned the corresponding APR, and wherein the conditions in the LOC are ordered according to likelihood.

5. The method according to claim 4, wherein the number of categories of discrete a priori ratings is between 3 and 5.

6. The method according to claim 4, wherein the number of discrete likelihoods is between 4 and 8.

7. A method for assisting a user in determining a medical condition in a subject from one or more medical images, the method comprising the steps:
   i) outputting to the user a list of foundation observations, LFO, from a database, wherein the database contains:
      a multitude of observations, MO, each corresponding to a description of a medical-image- or subject-related observation,
      a set of foundation observations, SFO, corresponding to a predefined subset of the MO, and used to generate the LFO, wherein the observations in the SFO are pre-defined patterns in the one or more medical images,
      a multitude of conditions, MC, each linked to at least one foundation observation,
      a multitude of rules, MR,
      wherein each rule in the MR links a discrete likelihood of at least one condition with the absence or presence of at least one observation,
   ii) receiving an input of a selection of at least one FO from the LFO,
   iii) generating:
      a set of conditions, SC, from the MC, wherein conditions not linked to the selected FO are excluded,
      a set of rules, SR, from the MR, wherein rules that are not linked to the presence of the selected FO are excluded, and
      a set of observations, SO, from the MO, wherein observations not linked to rules present in the SR are excluded,
         wherein a plurality of conditions in the SC is linked to a plurality of foundation observations in the SO by discrete a priori ratings, APRs, wherein each foundation observation is linked to the corresponding condition by one APR,
   iv) generating and outputting a list of conditions LOC from the SC, and a list of questions, LOQ from the SO, wherein each condition in the LOC is initially assigned the corresponding APR,
   v) receiving an input as to the status of one question in the LOQ whereby the status is an indication of the presence, absence or unknown status in regard of the subject,
   vi) updating and outputting:
      the LOC, wherein likelihood(s) for condition(s) linked to the rules satisfied by status received in step (v) are provided, the likelihood(s) replacing the APR initially assigned to the same condition in step (iv), and
      the LOQ, wherein at least the question corresponding to the observation status received in step (v) is removed,
   vii) repeating steps v) to vi) such that the LOQ iteratively reduces in length optionally until there are no more questions in the LOQ.

8. The method according to claim 7, wherein the number of categories of discrete a priori ratings is between 3 and 5.

9. The method according to claim 7, wherein the number of discrete likelihoods is between 4 and 8.

10. A method for assisting a user in determining a medical condition in a subject from one or more medical images, the method comprising the steps:
   i) outputting to the user a list of foundation observations, LFO, from a database, wherein the database contains:
      a multitude of observations, MO, each corresponding to a description of a medical-image- or subject-related observation,
      a set of foundation observations, SFO, corresponding to a predefined subset of the MO, and used to generate the LFO,
      a multitude of conditions, MC, each linked to at least one foundation observation,
      a multitude of rules, MR,
      wherein each rule in the MR links a discrete likelihood of at least one condition with the absence or presence of at least one observation,
   ii) receiving an input of a selection of at least one FO from the LFO,
   iii) generating:
      a set of conditions, SC, from the MC, wherein conditions not linked to the selected FO are excluded,
      a set of rules, SR, from the MR, wherein rules that are not linked to the presence of the selected FO are excluded, and
      a set of observations, SO, from the MO, wherein observations not linked to rules present in the SR are excluded,
         wherein a plurality of conditions in the SC is linked to a plurality of foundation observations in the SO by discrete a priori ratings, APRs, wherein each foundation observation is linked to the corresponding condition by one APR,
   iv) generating and outputting a list of conditions LOC from the SC, and a list of questions, LOQ from the SO, wherein each condition in the LOC is initially assigned the corresponding APR,
   v) receiving an input as to the status of one question in the LOQ whereby the status is an indication of the presence, absence or unknown status in regard of the subject,
   vi) updating and outputting:
      the LOC, wherein likelihood(s) for condition(s) linked to the rules satisfied by status received in step (v) are provided, the likelihood(s) replacing the APR initially assigned to the same condition in step (iv), and
      the LOQ, wherein at least the question corresponding to the observation status received in step (v) is removed,
   vii) repeating steps v) to vi) such that the LOQ iteratively reduces in length optionally until there are no more questions in the LOQ,
   wherein two or more observations in the SO constitute a subset of observations, SSO, such that the presence or absence of one observation of the SSO is indicative of the presence or absence of the remaining observations in the SSO.

11. Method according to claim 10, wherein the updated LOQ in step vi) is devoid of all questions enquiring as to the status of the observations in the SSO, when the answer received in step ii) is an indication of the status of one observation of the SSO.

12. The method according to claim 10, wherein the number of categories of discrete a priori ratings is between 3 and 5.

13. The method according to claim 10, wherein the number of discrete likelihoods is between 4 and 8.

14. A method for assisting a user in determining a medical condition in a subject from one or more medical images, the method comprising the steps:
   i) outputting to the user a list of foundation observations, LFO, from a database, wherein the database contains:
      a multitude of observations, MO, each corresponding to a description of a medical-image- or subject-related observation,
      a set of foundation observations, SFO, corresponding to a predefined subset of the MO, and used to generate the LFO,
      a multitude of conditions, MC, each linked to at least one foundation observation,
      a multitude of rules, MR,
      wherein each rule in the MR links a discrete likelihood of at least one condition with the absence or presence of at least one observation,
   ii) receiving an input of a selection of at least one FO from the LFO,
   iii) generating:
      a set of conditions, SC, from the MC, wherein conditions not linked to the selected FO are excluded,
      a set of rules, SR, from the MR, wherein rules that are not linked to the presence of the selected FO are excluded, and
      a set of observations, SO, from the MO, wherein observations not linked to rules present in the SR are excluded,
         wherein a plurality of conditions in the SC is linked to a plurality of foundation observations in the SO by discrete a priori ratings, APRs, wherein each foundation observation is linked to the corresponding condition by one APR,
   iv) generating and outputting a list of conditions LOC from the SC, and a list of questions, LOQ from the SO, wherein each condition in the LOC is initially assigned the corresponding APR,
   v) receiving an input as to the status of one question in the LOQ whereby the status is an indication of the presence, absence or unknown status in regard of the subject,
   vi) updating and outputting:
      the LOC, wherein likelihood(s) for condition(s) linked to the rules satisfied by status received in step (v) are provided, the likelihood(s) replacing the APR initially assigned to the same condition in step (iv), and
      the LOQ, wherein at least the question corresponding to the observation status received in step (v) is removed,
   vii) repeating steps v) to vi) such that the LOQ iteratively reduces in length optionally until there are no more questions in the LOQ,
   wherein two or more observations in the SO constitute a linked set of observations, LSO, associated to a status of a linking observation, and the LSO is used to generate a corresponding linked set of questions LSOQ enquiring as to the status of the LSO, such that an indication of a status of the linking observation initiates outputting the LSOQ enquiring as to the status observations of the LSO.

15. The method according to claim 14, wherein the number of categories of discrete a priori ratings is between 3 and 5.

16. The method according to claim 14, wherein the number of discrete likelihoods is between 4 and 8.

17. A method for assisting a user in determining a medical condition in a subject from one or more medical images, the method comprising the steps:
  i) outputting to the user a list of foundation observations, LFO, from a database, wherein the database contains:
    a multitude of observations, MO, each corresponding to a description of a medical-image- or subject-related observation,
    a set of foundation observations, SFO, corresponding to a predefined subset of the MO, and used to generate the LFO,
    a multitude of conditions, MC, each linked to at least one foundation observation,
    a multitude of rules, MR,
      wherein each rule in the MR links a discrete likelihood of at least one condition with the absence or presence of at least one observation,
  ii) receiving an input of a selection of at least one FO from the LFO,
  iii) generating:
    a set of conditions, SC, from the MC, wherein conditions not linked to the selected FO are excluded,
    a set of rules, SR, from the MR, wherein rules that are not linked to the presence of the selected FO are excluded, and
    a set of observations, SO, from the MO, wherein observations not linked to rules present in the SR are excluded,
      wherein a plurality of conditions in the SC is linked to a plurality of foundation observations in the SO by discrete a priori ratings, APRs, wherein each foundation observation is linked to the corresponding condition by one APR (FIG. 7 A2),
  iv) generating and outputting a list of conditions LOC from the SC, and a list of questions, LOQ from the SO, wherein each condition in the LOC is initially assigned the corresponding APR,
  v) receiving an input as to the status of one question in the LOQ whereby the status is an indication of the presence, absence or unknown status in regard of the subject,
  vi) updating and outputting:
    the LOC, wherein likelihood(s) for condition(s) linked to the rules satisfied by status received in step (v) are provided, the likelihood(s) replacing the APR initially assigned to the same condition in step (iv), and
    the LOQ, wherein at least the question corresponding to the observation status received in step (v) is removed,
  vii) repeating steps v) to vi) such that the LOQ iteratively reduces in length optionally until there are no more questions in the LOQ,
  wherein step ii) further comprises presenting the user with a series of choices, arranged in increasing specificity, to guide the user towards a selection of an indication of the FO present in the patient.

18. The method according to claim 17, wherein the number of categories of discrete a priori ratings is between 3 and 5.

19. The method according to claim 17, wherein the number of discrete likelihoods is between 4 and 8.

20. A method for assisting a user in determining a medical condition in a subject from one or more medical images, the method comprising the steps:
  i) outputting to the user a list of foundation observations, LFO, from a database, wherein the database contains:
    a multitude of observations, MO, each corresponding to a description of a medical-image- or subject-related observation,
    a set of foundation observations, SFO, corresponding to a predefined subset of the MO, and used to generate the LFO,
    a multitude of conditions, MC, each linked to at least one foundation observation,
    a multitude of rules, MR,
      wherein each rule in the MR links a discrete likelihood of at least one condition with the absence or presence of at least one observation,
  ii) receiving an input of a selection of at least one FO from the LFO,
  iii) generating:
    a set of conditions, SC, from the MC, wherein conditions not linked to the selected FO are excluded,
    a set of rules, SR, from the MR, wherein rules that are not linked to the presence of the selected FO are excluded, and
    a set of observations, SO, from the MO, wherein observations not linked to rules present in the SR are excluded,
      wherein a plurality of conditions in the SC is linked to a plurality of foundation observations in the SO by discrete a priori ratings, APRs, wherein each foundation observation is linked to the corresponding condition by one APR,
  iv) generating and outputting a list of conditions LOC from the SC, and a list of questions, LOQ from the SO, wherein each condition in the LOC is initially assigned the corresponding APR,
  v) receiving an input as to the status of one question in the LOQ whereby the status is an indication of the presence, absence or unknown status in regard of the subject,
  vi) updating and outputting:
    the LOC, wherein likelihood(s) for condition(s) linked to the rules satisfied by status received in step (v) are provided, the likelihood(s) replacing the APR initially assigned to the same condition in step (iv), and
    the LOQ, wherein at least the question corresponding to the observation status received in step (v) is removed,
  vii) repeating steps v) to vi) such that the LOQ iteratively reduces in length optionally until there are no more questions in the LOQ,
  wherein
    the medical image-related observations comprise the recognition of a morphological pattern from a medical image and/or
    the patient-related observations comprise age, gender, symptoms, medical history, laboratory results, or a combination thereof.

21. The method according to claim 20, wherein the number of categories of discrete a priori ratings is between 3 and 5.

22. The method according to claim 20, wherein the number of discrete likelihoods is between 4 and 8.

* * * * *